US006503706B1

(12) United States Patent
Abken et al.

(10) Patent No.: US 6,503,706 B1
(45) Date of Patent: *Jan. 7, 2003

(54) METHOD FOR IDENTIFYING HUMAN AND ANIMAL CELLS HAVING AN UNLIMITED PROLIFERATION OF TUMOR-FORMATION POTENTIAL

(75) Inventors: Hinrich Johann Abken, Meudt-Dahlen; Winfried Albert, Eberfing; Herbert Jungfer, Starnberg, all of (DE)

(73) Assignee: Roche Diagnostics GmbH, Mannheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/585,593

(22) Filed: Jan. 16, 1996

Related U.S. Application Data

(63) Continuation-in-part of application No. PCT/EP94/02307, filed on Jul. 13, 1994.

(30) Foreign Application Priority Data

Jul. 15, 1993 (DE) .......................................... 43 23 727

(51) Int. Cl.[7] .......................... C12Q 1/68; C07H 21/04
(52) U.S. Cl. ...................... 435/6; 536/23.5; 536/24.31
(58) Field of Search ........................... 435/6, 91.2, 174, 435/320.1, 240.2, 252.3, 254.2, 172.3; 530/300

(56) References Cited

U.S. PATENT DOCUMENTS 5,674,723 A * 10/1997 Abken et al. ............ 435/172.3

OTHER PUBLICATIONS

Abken et al. PNAS 90: 6518–6522, 1993.*
Abken et al., *The New Your Academy of Sciences*, 1993, vol. 684, "A DNA–Binding Zinc–Protein Increases the Immortalizing Activity of Extrachromosomal DNA Sequence from Mouse L929 Cells", pp. 193–195.
Derwent Publication, 86–115284.
Abken et al., *Proc. Natl. Acad. Sci. USA*, vol. 85, pp. 468–472, Jan. 1998, Immortalization of Human Lymphocytes by Transfection with DNA from Mouse L929 Cytoplasts

* cited by examiner

*Primary Examiner*—Lisa B. Arthur
(74) *Attorney, Agent, or Firm*—Arent Fox Kintner Plotkin & Kahn

(57) ABSTRACT

The invention addresses DNA-protein-complexes, proteins, DNA sequences and antibodies that are suitable for the detection of cells with an unlimited proliferation and tumor-formation potential. The invention further addresses methods for obtaining such proteins or DNA sequences and methods for identifying animal and human cells with with an unlimited proliferation and tumor-formation potential using such proteins, DNA sequences or antibodies.

26 Claims, No Drawings

SEQUENCE LISTING (1) GENERAL INFORMATION:

(iii) NUMBER OF SEQUENCES: 66

(2) INFORMATION FOR SEQ ID NO:1:

(i) SEQUENCE CHARACTERISTICS:
      (A) LENGTH: 203 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

```
GATCTTGAGT TTCCTCGTTG TAGGTCTTCC CTGGCTCTGC TCACGCTCTC ACTGACTTCT      60

CTCAGCTCAG TCACAGTGTC TATTTCTTTC CACTTAAAGA TGTGCATTTT TATTTGATGC     120
```

GTGCAGGTGT TTTGCCTGCA TGGATGGCTG TGCACCATGT ATGGGACCTG GTGCTCTTGG      180

AGGCCAGCAG AGGGCTTTGG ATC      203

(2) INFORMATION FOR SEQ ID NO:2:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

GATCTTTTCT TGAAAGTACG TAAGCCTGGG GTTTTAATTC TCATCTTAGA ACACAGTGTA      60

AAAAGGATC      69

(2) INFORMATION FOR SEQ ID NO:3:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

GATCTTCAGT GTCCATACAC TCAGATTCCT GATTAAATCA AAGCATCAGA ACCACTCCCC      60

CTGCAAAATG TCCCAAAATG TAAAATCAAT TGATGTACAA CTCAGAATAC ACCACTCTGA      120

GGCATATTTT CCAGGGACTC TAACCTACTT CAGAAGTACA TGGTACTTGC TTCTCTATTA      180

CAGCATAATA GAGATGAGCA ACATAGTGCA CTTACAAACA GATC      224

(2) INFORMATION FOR SEQ ID NO:4:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

GATCAGACCT CTACCTTCAC CCATGAGGCT TGCTTGCAGC AATTAAGATC      50

(2) INFORMATION FOR SEQ ID NO:5:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

GATCTTTAGC TCCCTGGATA CTTTCTCTAG CTCCTCCATT GGGGGCCCTG TGATC      55

(2) INFORMATION FOR SEQ ID NO:6:

(i) SEQUENCE CHARACTERISTICS:
        (A) LENGTH: 72 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO:6:

GATCTTTCCA AGACTTTTAT CATGAATGGG TGTTGGATCT TGTCAAATGC TTTTTCTGCA      60

TCCAACGAGA TC                                                         72

(2) INFORMATION FOR SEQ ID NO:7:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:7:

GATCCTGGCA TTACCCTATC CTGCATTAAG GGGGGAACAG GAAGATC                    47

(2) INFORMATION FOR SEQ ID NO:8:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:8:

GATCCATTCT ATCTCCACCC CCACCATGAG GATC                                  34

(2) INFORMATION FOR SEQ ID NO:9:

(i) SEQUENCE CHARACTERISTICS:
            (A) LENGTH: 176 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:9:

GATCTTCGCC GCCGACCTGA CCTCGATCGA GGTGGCGCNN GGCGTCGATC ATATCATCTT      60

TGGCTGGGTG TTCTTCGCGC TGGTGATGGC AGCGGTGCTG GCCATCGGCT GGCAGTTTTT     120

CGATCGTTCC CCCGATGATC CCATCACTGG CCAGGCATGG AGGCCCACAG GGGATC         176

(2) INFORMATION FOR SEQ ID NO:10:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:10:

GATCACGCCG GACGAAGCCT ACGACATCAC CGTCTACCAG ATC                        43

(2) INFORMATION FOR SEQ ID NO:11:

(i) SEQUENCE CHARACTERISTICS:
            (A) LENGTH: 42 base pairs (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GATCTCCTCG CCTCTCTATC CCCAGCACCT GCCAAGAGGA TC                42

(2) INFORMATION FOR SEQ ID NO:12:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

GATCTGGTCG ATGCCGATTG CTGAGGTTGG TTGGTGCGGT GATTCCTGTT AATTTCCTTA    60

GAGGAGGGTG GGTTTGCAGT GTCATGAGAA TGGAGGGTCG GGATTTGATC              110

(2) INFORMATION FOR SEQ ID NO:13:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GATCAAAAAG CGTGGAAAAA TTTGAATGTC ATGTCGAGCT GGTATCGGCT TCTGGAATAC    60

CGAAAGGATC                                                          70

(2) INFORMATION FOR SEQ ID NO:14:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

GATCTGGGGC CAGTGATAGC CATCTCTGTN CCTGTATGTG CCCGGACATC CTGGGGATAA    60

AGAGAGATCC TTCATGTGGA GGAAGATC                                      88

(2) INFORMATION FOR SEQ ID NO:15:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

GATCTTTCCA AGACTTTTAT CATGAATGGG TGTTGGATCT TGTCAAATGC TTTTTCTGCA    60

TCCAACGAGA TGATC                                                    75

(2) INFORMATION FOR SEQ ID NO:16:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

```
GATCCGTCGT CGCTGCCGTG CRCCGCCTTG CCATGGGAAC CGTGTCTGGG CCCTGTGTCA      60

CAAGGTTCCC CCCGGGATGA CAACCGTTGT GATC                                 94
```

(2) INFORMATION FOR SEQ ID NO:17:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

```
GATCTAACCG TGGAAGGCAG CGCCAGAGAG ACTGAATCAG GAGGATC                    47
```

(2) INFORMATION FOR SEQ ID NO:18:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

```
GATCTGAGTT CGAGGCTAGT CTGGTCTACA GAATAAGTTC CAGGACAACC AGGGCTGCAC      60

AGAGAAATCC TGCCTCCGGA AAGGAAAAAA GATC                                 94
```

(2) INFORMATION FOR SEQ ID NO:19:

(i) SEQUENCE CHARACTERISTICS:
        (A) LENGTH: 202 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

```
GATCTTGAGT TCCTCGTTG TAGGTCTTCC CTGGCTCTGC TCACGCTCTC ACTGACTTCT       60

CTCAGCTCAG TCACAGTGTC TATTTCTTTC CACTTAAAGA TGTGCATTTT TATTTGATGC     120

GTGCAGGTGT TTTGCCTGCA TGGATGGCTG TGCACCATGT ATGGGCCTGG TGCTGTTGGA     180

GGCCAGCAGA GGGCTTTGGA TC                                              202
```

(2) INFORMATION FOR SEQ ID NO:20:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

GATCCATGAC CACTCTTAGA AGCTGGTCTG GGTCTGAAGG GAAGGGGTCT TCAGAAGTCC    60

AGATGTGTGT GAACTGGATC    80

(2) INFORMATION FOR SEQ ID NO:21:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

GATCTGCTCT ATCTCAAATG GCATTCATTC CAGGCAGCCT ATGAAAGGAA CACTTGATC    59

(2) INFORMATION FOR SEQ ID NO:22:

(i) SEQUENCE CHARACTERISTICS:
        (A) LENGTH: 233 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

GATCAGCTCT CCTGCTCTCA GGACCCTAGG GCCAGGTCTC CTACCTGCAG CAGGTTATGA    60

GGAGTAAAGG GGTCTACCCC ACCATAAGGA GATGAGTATG CCAGTTCCCA TGTTCACATT   120

CTTGAGGACA GCTCACTTGT ATCTCCCATG TGAGGGCTC ACTCTAAGGA GTATTACAAC   180

TTGACTGTCA GGTGGCATCC AAGCATCTCT CTGCTGCTAC ATGGCCAAGG ATC          233

(2) INFORMATION FOR SEQ ID NO:23:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

GATCTCAGCT TTTGATAGAC TGAGGAAGAA GGGCCTCCTA GGGTACAAAT GTAAGTTTTA    60

TTCACCCGAG GTAATTTCCA GCTGCTAACC TGGAAGCTTC TACCCTCAGT AAAATCTTAC   120

CTAGACCTAG AATGTTTTTC AGCCTAAGAC TTATTGCAGA ATAATGCTCA CCCTTTCTAG   180

GTTCATTCTG TGCTGACTGG TCAACTCAGC TATGCAAATT GCTGACTGAC TTAAGCAGGT   240

TCTTCAGCTT GGACTGACGG CCCGCTTGGC CTCAGACTAC TT                     282

(2) INFORMATION FOR SEQ ID NO:24:

(i) SEQUENCE CHARACTERISTICS:
        (A) LENGTH: 125 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

```
GATCTTCATA AACGCGGGGT TCGGTCCCAG GGCTGGCACT CTGTCGTAGT ACCCCACCGA    60

GACCCCTATT AGGCCAATAC AGCACCGCGN NNCTTCCTTT TCCCCACCCC ACCCGGCCTA   120

TAGTT                                                              125
```

(2) INFORMATION FOR SEQ ID NO:25:

(i) SEQUENCE CHARACTERISTICS:
        (A) LENGTH: 118 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

```
GATCTTTGGC GCTGCGCAGA AGCCCAGTCC GAGGCGCGCG TCTTCGACCG GGACCGTGCT    60

CCGCGGCGNG CTGCCAGCCA AAGCCCAGGT CGACAGGTAG CCGTCGCGGA ACTCGATC     118
```

(2) INFORMATION FOR SEQ ID NO:26:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

```
GATCTGAGCA AAAGTTTTCA AAATTCTGGA ATTAGAAAAT TTGAAGGTCG AAAATACTTA    60

TATGGAACAT GAAGGACTGT GCTTTACACT TATGTGGTTT GTTGTTGTTT ATCTGTTATG   120

GTTTTGTTTT TGCTTTGTTT TGTTTTTCTG GTGCTGCACA TAGGCCCTGA AGAAGCTTGG   180

TTGCCGAGAC AAGCCACCAC AGCACACGGA ACTCCAGGGC TACTCTGATC CTATTTTTTC   240

ATCCATTCAG TTAGCCTGAA TCTTTTTTAT TAGGGAATTG AGTCCATTGA TGTTGAGAGA   300

TATTAATGAC CAATGATTGT TAATTCCTGT TATTTTGATG GTGGTGGTAG TAGTGTGTGT   360

GTGTGTATGT GTGTGTGTAG TATTTCCCTT CTTTTGGTTT TGCTGATGTG ATATTTATTT   420

CATGTTTTCA TGGGTGTACT TAATCTTCTT GGGTTGGAGT TTTCCTTCTA CTAGGGATAA   480

ATTTGTGGAC AGATATGGTT                                              500
```

(2) INFORMATION FOR SEQ ID NO:27:

(i) SEQUENCE CHARACTERISTICS:
        (A) LENGTH: 592 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

```
GATCCCGGAC TAGGATTAGC CTGTCTATGC CAGCAAATGA GTCAGGCAAC TGATGGTGAG    60

TCCTTCAGGT GTATATGTGT GGACAATTAA TTTTTATTAA AAAAATAAAT AAAGCCAAAG   120

GGAAATGTAT ATTTTAATGA CCTAGGGTAT TAATTTTTTT GAAAGTCACA CATCAAAGAC   180

TAGGAAAAGC CACCAACACC CTAAGAATGT GATTTTATCC TTTTTCCTCT GTGTGGGATG   240

TGTTTTAGTT TAGGTTTCTT TCTGTTTCAA TTTGGACCTG TAGAGGAATG ACCGTCACTG   300

TCTTATTCTG GAGGGAAGTC CCTGATAGTG CCCCACTACA CACACACACA CACACATACA   360
```

| | |
|---|---|
| CACACACAAA TTAGGTATTA AAATATGGTT TTAAGAGTTT TAAAAATGGA TTAGCAGTGA | 420 |
| TTCAATTAAA ATTAGAAAAG AACAACAACA AATATGTGAG AGACTTGCCT CTCAGTGACC | 480 |
| CCAGGCCCTG TCAGCTGATA GTGGGTGGTA ACCAGACAGC CCATTTCTGT GTCGATAGAT | 540 |
| GAACTGTGGG AGAGTGACTC CAGAAAGAAC CAACCAGTGA GGGGTCGAGA TC | 592 |

(2) INFORMATION FOR SEQ ID NO:28:

(i) SEQUENCE CHARACTERISTICS:
        (A) LENGTH: 255 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

| | |
|---|---|
| GATCCCTTTA GCTCCTTGGG TTCTTTCTCT AGCTCCTCCA TTGGGAGCCC TGTGATCAGC | 60 |
| CTGTACCACA TAGCAAATGT CAGGCCTCTT GGGGAGTAT TGCAAGATAT TGCTACAAAT | 120 |
| AACAACAAAA GCAAACAAAG TTAACGTTTG CATAGCAACC TCCACCCCCC CAAGATTATA | 180 |
| CCTGTACATA ATTTATGTTC AAAGACAGTG GCACAGGTCT GGCAAGATGC CTCACTTGAG | 240 |
| AGAAGCTCAC AGATC | 255 |

(2) INFORMATION FOR SEQ ID NO:29:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

| | |
|---|---|
| GATCCAATCA GCTCAGCCAC CCCCAGCTCT CCTGTATGTA TGGCTCCAAT GCTGTTCATC | 60 |
| CCTCAGCATA AATCAATCAT TTGGTTTAGA TTCCTCCCTT TGACTTATTG CTACTATTAG | 120 |
| TATCAGTGAC TCTTCAGCCG ATTCTTTTCA GACATTGGAA CCCCAGCCTC AGATCACAGT | 180 |
| TGTAGAACAA ATATTAAAAG AGTAAATTAT TATATCATTG AACATTCAAA AGTGCTTTGC | 240 |
| AGTCATTGAC ACATAATAAT AATGAAGCCT AAACAGTAAC ATGAAAATGT GGAATTGTAT | 300 |
| TAATGTAAAA TCAAGGCCTG GGGNATAGCT CATTGGTGGA TGTTTGGCTA TCATGTGGGA | 360 |
| GGGCCTGGTT TT | 372 |

(2) INFORMATION FOR SEQ ID NO:30:

(i) SEQUENCE CHARACTERISTICS:
        (A) LENGTH: 128 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

| | |
|---|---|
| GATCTTGTCA AATGCTTTTT CTGCATCCAA CGAGATGATC CAACACCCAT TCATGATAAA | 60 |
| AGTCTTGGAA AGATCATGGC GACCACACCC GTCCTGTGGA TCCACAGGAC GGGTGTGGTC | 120 |
| GCATGATC | 128 |

(2) INFORMATION FOR SEQ ID NO:31:

(i) SEQUENCE CHARACTERISTICS:
    (A) LENGTH: 184 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:31:

```
GATCAGCAAC AGATTACTAC GAAAAGGCAA GCAAACAAAC AATAACAATA ACAAAACAAA      60
CCACTGTGTT GGATTTACTG ACTGCCTGAA ACAAATTACC CAAAGTATAG ACCTCAAAAT     120
ATCCATGTGA ACAGGGAAAC AAAGCACACA GACGAGCAAA AGTGGTCTCG AGGTGCTTAT     180
GATC                                                                  184
```

(2) INFORMATION FOR SEQ ID NO:32:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

```
GATCTAATAC CAATACTCTT CAAACTATTC CACAAAATAG AAACAGAAGG AACACTACCC      60
ATTCATTCTA TGAAGCCACA TTTTTGCCAT GTATTCTCCC TTCAAAATGG AAAGGTTTCT     120
GTCTAATCAG GAACTTGTCA CAATTTCCTT TCTTGGAGGA CTTCATAAGA GATTTTTTC      180
TACTTCTACC ACATTTAAGA TTCCAAACAG ATTTTAAACG GTTGTGTTCA TATTACTTTA     240
GTTCAGAAGA TATCATGTAT ATATAAGAGG CATTTAACAA TTATAAATTA TTTGGATGAC     300
TTAAAAATAT CAATACTGAG TTGTATATTT TAAAATAAAT TTTATTGGTT TTAAAAAAAC     360
AACCATAGGA TC                                                         372
```

(2) INFORMATION FOR SEQ ID NO:33:

(i) SEQUENCE CHARACTERISTICS:
        (A) LENGTH: 184 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

```
GATCTCAGTT TTTAAAAATA AAGAAAATGC ATTCTTTTCA GAAGGAACAT GAAGATCTAG      60
AAGAAGTTCT GTGGCTAGAT GGATTTTGAA AGGTCCCGAA AGGTCCCGAA AGGTCCGGGG     120
GNNGCCTGCT TCATGACTGT CACACACTTC AGTTGTCCAG GGAAGAGATA GAAAATGTGT     180
GATC                                                                  184
```

(2) INFORMATION FOR SEQ ID NO:34:

(i) SEQUENCE CHARACTERISTICS:
        (A) LENGTH: 385 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

```
GATCTCGCCT TGCAGATTTT TTTACCAACT GCCAGCCAGA GTCAAGGTCT GTCAGCAACT      60

GTCTTAAGGA GAACTACGCA GACTGCCTCC TGGCCTACTC GGGACTGATT GGTAAGACCA     120

GGGGAGGGAG GGAATGGCAA AGAAATCTGG ATTACAGATC AAGATGGGAC AGTTTAGCTT     180

CTGGTGACAG GCTAGATCCG ATGCCCTCTT CTGGTGTGTC TCAAGACAGC TACAGTGTAC     240

TTATATACAT AAAGTAAATA AATATTTTAA ACAAAACTTT TAAAAAAAAA AAGATTGGCT     300

ACAAAACTGA CCTATAGGGC TCCTAGCAGT CCTTGTCACC ACATAGCTGC AAACCCACCT     360

AGGGGAAAAC TGAGGCAGGA GGATC                                          385

(2) INFORMATION FOR SEQ ID NO:35:

(i) SEQUENCE CHARACTERISTICS:
        (A) LENGTH: 371 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

GATCTAACTT CCCTGTCCTG ATTGCTTTCA TGTAGAAACA TTCTGCAGCC AGAAGTGGCA      60

GCACACAGCC CCGGTCCCCA CATCTGGGAG TCTGAGATAG ATGGAGCCTA AGTTTGAGAA     120

CTAAGTACTT TACAATTGCA GGCATAATTG AAATTGAGCT GCCTTCTGTG TCTTCTGGAC     180

AAAGTTAACG TGATTTATAG GAAGGCATTC TGTGATCCTT TTCTGGTTGC ACCATCCTGT     240

TCTCTCCAGG CCTGTGAATC ACAGCACACC AGTCCACATG TGCCTGCGCT GCTCTGTTGT     300

GGCAAGTGCT CCATCAGACT GGGATTTCTC TGCCAGGAAG GCAGGCTGGT CCCAGGCTAC     360

TTAGGAAGAT C                                                          371

(2) INFORMATION FOR SEQ ID NO:36:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

GATCTAGAGA GGTTAGGTAA AGAGTAGAGC TATAAATATA AGCCTGGGTT TCCCTGGGAA      60

GGAGTATTAA TTAGACTAGA TTCTCCATGA GCTGGGGAAG GGGGTAGAGG GNNGGGGAAG     120

GGAAGAAGAC AGGAACAGGA GAGATATTGT GTGTATGTAT GTGGTGGGGT GGTGGAGGGA     180

AAGAGTGTAG NNGACTGGCA GTCAGATTGG GAGGCATTGA GTGATGTAGA ACTAGTGTGG     240

TAGAACTTGT GACTCTCTGA GTGTAACACT ATTGCAGACT CACTAATGGA GGATTCAGAG     300

TCTGATTTGT CACTTTTTGT AGTCAGGCAA GGCTTCCAGC GGAAGCTGTG GGCTACACTT     360

GATTGCGCTG TTGGCTGAGG AGGACCCATG GAGATC                               396

(2) INFORMATION FOR SEQ ID NO:37:

(i) SEQUENCE CHARACTERISTICS:
        (A) LENGTH: 433 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:37:

```
GATCCAAGGG AGTGTTCCAG TTTTTCTGGA AGCTGAGATG CTCCAGCTGG TAGCTTGAGC        60
TTCACAAAGA TGCTGCCCTA ATAAATGTCA AGCACCCAGG GACTTCTCAG GAGCACATGC       120
TATGCTTAAA GGGGCCACAG TGAAATCTTA GACAAAGATG GATGGAGGTC TTGGCTTCTT       180
TTGTCTGTCT CTGTCTCATC TTTCTCTCTC TCTCTGTGGC CTGTATGTAT GCATGTGCCT       240
TGTGCCAAGG AGGGCAGAAA AGGGTGTTAG ATCCTCCTGC CTCAGTCTTC TACATGCTGG       300
TTTTGAAGGC TGGTGCCACC ATTCCCAGCT CTCAAACTTG CTCGTGCCTG TCCCCTTTAT       360
AGAGGATAAG TTAGCTAAAT TGGTTCTCAT TATCCTTCTG TTTTCTGGCT TTTGGACCAT       420
CAGTGGTTTG ATC                                                          433
```

(2) INFORMATION FOR SEQ ID NO:38:

(i) SEQUENCE CHARACTERISTICS:
        (A) LENGTH: 434 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

```
GATCTGTATA AAGCACAAGG AGGCTTTATC TGTCTGGACT CATCTGAGGA TTCTTTGGAT        60
CACTATTTAG ACATGTTAAA TTGATTAGAG AAGTCATTCA CTGTCATTGG GTACCATTTG       120
TCACATCATA AACAGCTGCA GTGTGCTGCC TCCAAATGCA GAAGGACCAA CAAATAAATC       180
ACATCAAATG GTGGGAGTAG ATGCTATCTT TCATCTATAA TTGGTATAGC CTTTCCTGTC       240
ACATTGCTCA TTCTTATGAT TCTAGTGTGA TTGACAGACA GGGAAAGGGC AGCCTCTGTC       300
AAAGATGTTC AGAGAGTGTG TGTTCGGGTG ATGTACCTGC TAATAGATAT CCATCATAAT       360
ATTACATTAA TGTCACCATG CATCAAACAT ACAACTTACC CATCTAGGTA TCTGATGTTA       420
GACCCATAAG GATC                                                         434
```

(2) INFORMATION FOR SEQ ID NO:39:

(i) SEQUENCE CHARACTERISTICS:
        (A) LENGTH: 128 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

```
GATCCAGCTA CAAATCTCAC AAAACACTCT GCCTGGGACA GAGGGTGTGA GTTGTAGTGG        60
TCTGAGGCAG GAAGCTCTGA GGCAGGGCTA GAAGAATTAC CTTGGAATTA CCTTCAGAAG       120
ACAGGATC                                                                128
```

(2) INFORMATION FOR SEQ ID NO:40:

(i) SEQUENCE CHARACTERISTICS:
        (A) LENGTH: 185 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

```
GATCAGCAAC AGATTACTAC GAAAAGGCAA GCAAACAAAC AATAACAATA ACAAAACAAA         60

CCACTGTGTT GGATTTACTG ACTGCCTGAA ACAAATTACC CAAAGTATAG ACCGCAAAAT        120

ATCCATGTGA ACAGGGAAAC AAAGCACACA GACAGAGCAA AAGTGGTCTC GAGGTGCTTA        180

TGATC                                                                    185
```

(2) INFORMATION FOR SEQ ID NO:41:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

```
GATCAAGTGA CCATAGGTGT ATGGATTCAT CTCAGGGTCT TCAATTCTGT TCCATTGGTC         60

TACTTGTCTG TTGCCATACC AGTACCATGC ACTTTTTATC ACAAGTGCTC TGTAGTACAG        120

CTTTAGATC                                                                129
```

(2) INFORMATION FOR SEQ ID NO:42:

(i) SEQUENCE CHARACTERISTICS:
        (A) LENGTH: 275 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:

```
GATCTGACAC CCTCTCTGGT CTCTCTGGGC ACTGTGCTCA CGTGCTCCTC AACTCCCATN         60

ACACGGAATT AAGAATCAAA ATATAAAATC TATAAAAAGA AAGGAAGGAA GGAAGGAAGG        120

AAGGAAGGAA GGAAGGAAGG AAGGAAGGAA GGCAGGTAGG CAGACAGGAA GAAAGAAAGA        180

AGAAAGAAA GAAAGAAAGA GAGAGAGAGA GAGAGAGAGA GAGAGAAGAA GAAGAAGAAG        240

AAGAAGAAGA AGAAGAAGAA GAAGAAGAAG AAGAA                                   275
```

(2) INFORMATION FOR SEQ ID NO:43:

(i) SEQUENCE CHARACTERISTICS:
        (A) LENGTH: 225 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:43:

```
TCCACATTCT CCTTTGCTCT ATTATCCTTT CCTTTCCACT ACCACTGGTG AGTGATGGGC         60

TAGAGGTTAA AGCTTATATA AACTCTTATT TAAAATAAGT TTTAAAAAAT TTAAGTCTAT        120

AAAAGCCAGG AAAAGCAACC AATAATCAGC ATTCTTCCAT GGCCTCTGCT TCAGTTTCTG        180

CCTCGAAGTT CCTGCCTTGA CTTCCCTCAT TAATGCAACA TGATC                        225
```

(2) INFORMATION FOR SEQ ID NO:44:

(i) SEQUENCE CHARACTERISTICS:
        (A) LENGTH: 403 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO:44:

| GATCTGGCCT | CCCTCTTCTT | GCCTTTGCAA | GAACTCTATG | TACATGATAT | GTGTACACAT | 60 |
| GCAAGCAAAA | TACCCATGCA | CACAAAATAA | GGGGGTGGGA | GGAACAGTCC | CAGAGCGAAT | 120 |
| GCGTGAATTA | AGACAAGCCA | GGTGTAGTGG | CACAGCTCTG | TGGTCCTAAT | GCTTGGAGAA | 180 |
| TATAATCAGG | AGGATTTCTA | GCTCAGTGTA | TAACAAGACC | TTCTCCTAAG | AGAATAAAAA | 240 |
| TAGATGTAAA | TATAAATAAA | TAAACATAAA | ATAAGACAAT | TTGTAAACTC | CTTATGAGAA | 300 |
| CTTGCTGTGG | CTTTACTGGT | ACATAGACCA | GTAAGATTTC | AGTGTAAAAG | ACGCTCTCTG | 360 |
| TAAAGGGTGA | GNCAAAGGGT | CCAGGAGAGG | CTTTCCTTAG | ATC | | 403 |

(2) INFORMATION FOR SEQ ID NO:45:

(i) SEQUENCE CHARACTERISTICS:
        (A) LENGTH: 543 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:45:

| GATCTGAAAT | TTTGAATATA | TAAATAACTA | ATCTTTACTA | CCTTTAGATT | GATGTCTTCC | 60 |
| AAGATGAGTA | TGGTTAAATA | ATATTCAAAA | ATCTGCATGC | TAAAGATTTG | TCTCAAGCAA | 120 |
| GTCACTGTTG | GGAAGTAGTT | ATATTGTAAG | AAGAAGTTGG | GTCATAAGGA | CACAGCTTGA | 180 |
| AAGGCAAAGT | AGGACTGCAC | CCACTTTCTC | AGCTTTTATA | TTGCTTCATG | ACTAGGAAAT | 240 |
| GAAAAGTTGT | CATGTGTCAC | CTATCATAGC | CATCCAGCAC | CCAAGTCAGT | GGCCAGAAGA | 300 |
| CAGTGTGTCA | GCTTGGGATG | GAATGGAATC | TCAAAACTGT | CAATCAAATT | AAACTGTGTG | 360 |
| TGTGGAGGGC | TGTATAAGTA | TGTACATGTG | AGTTTATGTT | TGTATGTACA | TAGATGCACA | 420 |
| TGTATGTGTG | TATATACATG | TGTATCATGT | GTGTGTGTGT | GTGTGTATGT | GTATGTGTGT | 480 |
| GTGTGTGTGT | GTGTGTGTGT | GTGTGTGTAG | TACAGAAATC | AATCATGGGC | ATTATTCCTG | 540 |
| ATC | | | | | | 543 |

(2) INFORMATION FOR SEQ ID NO:46:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:46:

| CAAGAAATGC | TAGAGCTAGG | GTTCCTTTTA | AAATTGTCGA | TGTTTCTGAT | GAAAATTATT | 60 |
| ATCAAAAGAT | TAATAC | | | | | 76 |

(2) INFORMATION FOR SEQ ID NO:47:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:47:

GCCTTTATTT ATTACCAAAA AGAAAAGTAT TTTCTTTAAT TTGGAAGTTT TCACAAAAGG      60

CAATATCAAT ATTATATTGT AACATTTAAG AATTTTAAAG CCAGAAATTA AAGA           114

(2) INFORMATION FOR SEQ ID NO:48:

(i) SEQUENCE CHARACTERISTICS:
            (A) LENGTH: 88 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:48:

ACAGGATCAC TTGGGGACAT CTCAGGTAAC CGTGTTTTCA AAGGTATGAC ATGCCAGGTC      60

ACTTAGGAGC TGTTAGAACA ACAGTTCA                                        88

(2) INFORMATION FOR SEQ ID NO:49:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:49:

CTTTTTAAAG TAATTAGATT TGTAACATAA GGTATTTTAA GAAAATAAAT ATTTTGATTG      60

GTTAGT                                                                66

(2) INFORMATION FOR SEQ ID NO:50:

(i) SEQUENCE CHARACTERISTICS:
            (A) LENGTH: 105 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:50:

ATGTCAACAT TTTTTTCTTG AACTAGTGCT AATAGAAGAT CAAGTTGCCT TATTTTTAAA      60

ATAAAATTTA GTTAAAATTT TGTCAAAACC CTTTAATTTT ATTTT                     105

(2) INFORMATION FOR SEQ ID NO:51:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:51:

CCAGATTCTC TTGCTTTTTC AGCTGTTTTA TCAGTACAAT TATGTGCTAT AA             52

(2) INFORMATION FOR SEQ ID NO:52:

(i) SEQUENCE CHARACTERISTICS:
            (A) LENGTH: 202 base pairs (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:52:

```
CGGACCTATT ATCCTTAATG AATTACTTAA AGTTGCTGAC ACTCGTTCAG TTCAAAACTA      60

CTTATTGAAA GAAGTACAAA GACTTTATCG TCTTCAAGGT ATCACAATTA GTGATAAATA     120

TATTGAAATG ATTATTCGTC AAATGCTTTC AAAAATTGTT ATTACTGATC CAGGAGATAG     180

TAAATTCTTT AGTGGTAACT TA                                              202
```

(2) INFORMATION FOR SEQ ID NO:53:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:53:

```
AAGAAGATTA ACTTACAAAG ATTTTTTGGA AAAATATAAA CTTATTATGG ATAAAAATAC      60

TATTCTAAAA TTCAAATCAG ATAATGATAA ACTTTATGAA TTTTCATTAG AAAGCTTTAA     120

AGAAAACGAT AAATATAATT TCATATGGCA GAGATTTGCA TAAAAGCAAA                170
```

(2) INFORMATION FOR SEQ ID NO:54:

(i) SEQUENCE CHARACTERISTICS:
        (A) LENGTH: 188 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:54:

```
TTGAGTTTTA TTAGTTGAAG TTTTAAAGCG CTAGTACAAG AAAATTTTTC AGAAAACGTT      60

CTTATTGTAC TTTGAACGTG GTTGTAGAAA TTTAAAAAAC ACACTAGTTA TTTGAGGATT     120

CTGTAGTGAA GGCGGACATG AACTCAATTA ATAATAATTA TTTCGGCGAC GATAAGGACG     180

AACATTTT                                                              188
```

(2) INFORMATION FOR SEQ ID NO:55:

(i) SEQUENCE CHARACTERISTICS:
        (A) LENGTH: 230 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:55:

```
CTTTAACAAT TCTTACATTT AAAACTTCTA CTAATACATC TAAATGTTTT TTAACTCCAT      60

GGCTCGAGCT TAAGCATTAG TACCAGTATC GACAAAGGCA CACATTTAAC AATAGGCGAG     120

TGTTAAGGTG TGTTGTATGC TCGGCCTTCG TATTTCACAT TCGGACCCCA CGGATTACTC     180

ACTCGATTGA GTGTAATTAA CGCAACGCGA GTGACGGCGA AGTCAGCCTT                230
```

(2) INFORMATION FOR SEQ ID NO:56:

(i) SEQUENCE CHARACTERISTICS:
    (A) LENGTH: 139 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:56:

```
CACTTGTAGG TACTACAGTT GTAAAAAAAG AACTTGATCA CGATTATCTT CTAGTTCAAC      60

GGAATAAAAA TTTTATTTTA AATCAATTTT AAAACAGTTT TGGAAATTAG AAAATAAAAC     120

CCATGGCTCG AGCTTAGCA                                                  139
```

(2) INFORMATION FOR SEQ ID NO:57:

(i) SEQUENCE CHARACTERISTICS:
        (A) LENGTH: 225 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:57:

```
ACGTCCGTAC GTTCGAACCG CATTACTACC AGTATCGACA AAGGCACACA TTTAACAATA      60

GGCGATTGTT AAGGTGTGTT GTAAGCTCGG CCTTCGTATT TCACATTTCG GACCCCACGG     120

ATTACTCACT CGATTGAGTG TAATTAACGC AACGCGAGTG ACGGGCGAAA GGTCAGCCCT     180

TTGGACAGCA CGGTCGACGT AATTACTTAG CCGGTTGCGC GCCCC                     225
```

(2) INFORMATION FOR SEQ ID NO:58:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:58:

```
ACCTGCAGGC ATGCAAGCTT GG                                               22
```

(2) INFORMATION FOR SEQ ID NO:59:

(i) SEQUENCE CHARACTERISTICS:
        (A) LENGTH: 215 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:59:

```
CCCTAAAATT AAGAATTTA AAGAATTAGT TAAAAGCAGC AAAGAATTAT TCTTACAAAA       60

AATACAAGCA AAATTTGAAA TGACTAAAAC GAGATTCAAG AATCAAGCCT TGCATTGTTT     120

CAATAATCAA TTAGCAACTT TTTCAATAGT AAAAGAAAAA GTTATTCAAC GTAATCCATT     180

AAAATATTAG AAAGTTTCGA AGTTACAATG AACAC                                215
```

(2) INFORMATION FOR SEQ ID NO:60:

(i) SEQUENCE CHARACTERISTICS:
        (A) LENGTH: 192 base pairs (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:60:

TAATTGAAAA ACATGTTGAT GAAGTCGATA TGGTAGAAAA TTAAGTTACA TTTCAAAAAA      60

TAGTTGAAAT TGAACAAAAT AACAAAATTA ATAAACCAAC AAAAGTAAAC ATTGAAAACG     120

TTTTTGAAAA AGATTATAAA AATTACCTAA TGTAACTTAT TGAAAAAGAA AATGATAACT    180

TTTTCAACGA TT                                                        192

(2) INFORMATION FOR SEQ ID NO:61:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:61:

ATGACCAAAA TAAATTAACG TGAGTTTTCG TTCCACTGAG CGTCAGACCC CGTAGAAAAG      60

ATCAAAGGAT GTTCTTGAGA CCTTTTTTTC T                                    91

(2) INFORMATION FOR SEQ ID NO:62:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:62:

NNAAANTNTN GAANTGTANN ANTGNAA                                         27

(2) INFORMATION FOR SEQ ID NO:63:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:63:

GATCTTGAGT TTCCTCTGTG TAGGT                                           25

(2) INFORMATION FOR SEQ ID NO:64:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:64:

GATCCAAAGC CCTCTGCTGG CCTCC                                           25

-continued (2) INFORMATION FOR SEQ ID NO:65:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:65:

GATCCAATCA GCTCAGCCAC CCCCA                             25

(2) INFORMATION FOR SEQ ID NO:66:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:66:

AAAACCAGGC CCTCCCACAT G                                 21

METHOD FOR IDENTIFYING HUMAN AND ANIMAL CELLS HAVING AN UNLIMITED PROLIFERATION OF TUMOR-FORMATION POTENTIAL

This is a continuation-in-part of PCT Application No. PCT/EP94/02307, filed on Jul. 13, 1994, which designated the United States as a contracting state.

BACKGROUND OF THE INVENTION

The invention relates to DNA protein complexes, proteins, DNA sequences, and antibodies that are suitable for the detection of cells having an unlimited proliferation and tumor-formation potential; methods for obtaining such DNA protein complexes, proteins or DNA sequences and their use to identify animal and human cells having an unlimited proliferation and tumor-formation potential.

All differentiated human and animal cells have a limited in vivo and in vitro proliferation potential before they undergo aging (senescence) and cell death. The number of cell divisions that are possible at a given time depend on the degree of differentiation of a cell, its age, and the species of the donor from which the cell was obtained, and on the duration of the cell cultures (Goldstein, S.: Replicative Senescence, Science 249 (1990), 1129–1133). Unlimited proliferation, however, is frequently found in neoplastically transformed cells. They thus form constantly growing symplasms leading to the formation of a tumor and, finally, together with the altered characteristics of other properties of these cells to tumor diseases. As compared to benign tumors, these malignant tumors are clinically characterized by their rapid growth and frequent formation of metastases. A neoplastic transformation of the cell is characterized by a heterogeneous picture of numerous alterations of the cellular morphology and physiology which also depend on the degree of differentiation of the cells. To date, only few molecularly definable parameters of neoplastic transformation are known; they include, for example, an altered degree of methylation of certain genes (W. Doerfler et al., Eukaryotic DNA methylation: facts and problems, FEBS Letters 268 (1990), 329–330), modified gene expression, or altered phosphorylation of certain gene products.

What is common to most tumor cells is the capability of unlimited in-vivo proliferation. Based on various observation, investigators assume that the proliferation of tumor cells which is independent of growth factors is, indeed, a frequently occurring characterisitic of tumor-forming cells, but not an absolutely necessary one (M. Strauss, B. E. Griffin, Cellular Immortalization, Cancer Cells 2 (1990), 360–365). However, for many questions in the field of diagnostics and therapy, it is of critical importance to identify those cells which no longer obey normal proliferation control and, hence, have acquired the potential for unlimited proliferation.

The problem involved in this matter is to distinguish this property of unlimited proliferation of tumor cells from the capability to regenerate that is found in many tissues. Regeneration is a controlled, short (transient) cell replication and only a intermittent suppression of programmed cell death as a response to a physiological stimulation. The transient proliferation of normal cells is again inhibited after regeneration of the tissue by still unidentified signals.

Known methods for the detection of malignant tumor cells are based on clinical, histological, and cytological observations, and on altered physiological measurements. Based on histological examinations, diagnostic routine methods are usually done with tissue sections (W. A. D. Anderson and J. M. Kissane, Pathology I, II, Mosby, Saint Louis 1977, 7th edition; C. S. Herrington and J. O. D. McGee, Diagnostic Molecular Pathology, Oxford University Press, Vol. I, II, 1st ed., 1992). As opposed to benign growth, the group of malignant cells is only vaguely separated from adjacent tissue, and the cells grow into surrounding tissue which they infiltrate and destroy. Most cases are triggered by a perifocal inflammation. Frequently, a great number of mitoses indicate increased proliferation activities of the tumor cells.

In addition to these histological examinations, it has become more common to use antibodies to detect proliferating malignant cells which recognize antigens that are preferably expressed by proliferating tumor cells such as Ki67 (D. C. Matthews, F. O. Smith, I. D. Bernstein, Monoclonal antibodies in the study and therapy of hematopoietic cancers, Curr. Opinion Immunol. 4 (1992), 641–646; M. Schwouzen, V. Diehl, M. Pfreundschuh, Immunozytologische Phänotypisierung von Leukämien und Lymphomen, Med. Klinik 85 (1990), 533–547). However, these methods are based on the determination of indirect parameters without detecting the molecular processes that are linked to unlimited proliferation.

SUMMARY OF THE INVENTION

It is, hence, an object of the invention to identify cells with a potential of unlimited proliferation, especially malignant tumor cells, in a rapid and reliable manner without cultivating these cells in vitro or propagating them after injection in laboratory animals. It should be possible to distinguish between cells having the potential for unlimited proliferation and cells with transient proliferation in regenerating tissue.

This object is accomplished with a DNA protein complex (hereinafter referred to as complex) which is suitable for detecting human or animal having an unlimited proliferation and tumor-formation potential. Said complex can be obtained by isolating a mitochondria-free fraction of the cytoplasm from human or animal cells which can permanently divide and have a density of approx. 1.82–1.89 g/cm$^3$ in a cesium chloride gradient; this is followed by isolating the complex from this fraction by extraction with phenol and precipitation with ethanol.

Experience has surprisingly shown that cells having an unlimited proliferation and tumor-formation potential, as opposed to normal resting cells, senescent cells, or cells with transient proliferation do have such complexes in their cytoplasm. With these complexes in accordance with the invention it is possible to detect such cells, which exhibit unlimited growth potential as a consequence of malignantant growth. In order to accomplish this, one uses cytoplasm or a suitable cytoplasm fraction in a complex in accordance with the invention as a standard in a gel electrophoresis by determining the DNA contents or reaction with a specific antibody.

In order to isolate complexes of the invention, cytoplasts of human or animal cells that are permanently capable of dividing are obtained according to known methods (for example EP-B-0 093 436, EP-B-0 256 512 and Proc. Natl. Acad. Sci. 85 (1988), 468–472 and lysed for example using detergents like NP40 or SDS, Wigler and Weistein, Biochem. Biphys. Res. Commn. 63 (1975) 669–674). The mitochondria are separated from these cytoplast fractions, preferably with the aid of a sucrose gradient (J. Biol. Chem. 249 (1974) 7991–7995). Those fractions who do not contain any mitochondria are incubated with RNase, preferably RNase A and RNase T1 as well as with proteinase, e.g. proteinase K or pronase. A fraction from this mixture with a density of approx. 1.82–1.89 g/cm³ in a cesium chloride gradient is enriched, and from this fraction, a complex is isolated by extraction with phenol and precipitation with ethanol. A fraction which has a density of approx. 1.82–1.89 g/cm³ in a cesium chloride gradient can be obtained both by means of centrifugation with a cesium chloride density gradient and by means of electrophoretic separation; these methods are known to the expert in the field (Sambrook et al., Molecular Cloning, Cold Spring Harbor Laboratory, 2nd edition, 1989).

The mitochondria-free fraction of the cytoplasm that is used for isolating the complexes can also be obtained by repeated freezing and thawing of the cells or by obtaining a cell fraction which is free of nuclear DNA. Such a fraction is preferably obtained by lysis of the cell with sodium chloride and SDS ("Hirt extraction", J. Mol. Biol. 26 (1967) 365–369) followed by centrifugation. The complexes can then be isolated from the supernatant.

In a preferred method, the complexes are isolated via sedimentation from a cytoplasmatic lysate of the cells to be examined using a salt gradient. The cells are lysed in a $Mg^{2+}$-containing buffer (50 mmol/l Tris-HCl, pH 7.2, 10 mmol/l EDTA, 3 mmol/l $MgCl_2$) by repeated freezing and thawing without using a detergent; the nuclei are sedimented by centrifugation at 6000×g and the supernatant is digested with proteinase K (100 µg/ml) for 1 h at 60° C. The released complexes are isolated by centrifugation (150,000×g, 10 h) with the aid of a CsCl two-step gradient; the lower fraction has a density of approx. 1.80 g/cm³ while the upper fraction has a density of approx. 1.70 g/cm³. The cytoplasmic complexes will sediment while the chromosomal DNA or complexes without covalent DNA protein binding will remain in the supernatant.

This method allows a very rapid isolation of cytoplasmatic complexes utilizing the following properties:

The complexes are released by freezing and thawing a $Mg^{2+}$-containing buffer without lysing the nucleic or using detergents.

The complexes are stable with respect to proteinases while cytoplasmic organelles and membranes are digested.

The complexes have a very high density (approx. 1.86 g/cm³) and can be separated from chromosomal or other cytoplasmic DNA with the aid of salt gradients.

The DNA protein binding is stable with respect to high salt concentrations.

The complexes can be obtained from cytoplasm of any transformed cell, particularly permanently growing human animal cells, or from tumor cells, especially those that were obtained from tumor biopsies. Transformed cells are understood to be those that are rendered immortal by adding an agent. Permanently proliferating cells of different species (e.g. human, mouse, rat) and cells of different degrees of differentiation (fibroma, myeloma, ascites cells) contain complexes which differ with respect to their protein and/or DNA contents. The complexes of the invention are, hence, specific with respect to species and degree of differentiation. For the detection of cells having an unlimited proliferation and tumor-formation potential, one isolates complexes from cells of identical species or cell types similar to the one to be examined. For the detection of mouse fibroblasts/fibroma cells or mouse ascites tumor cells with unlimited proliferation, it is particularly preferred to use complexes that were isolated from the cytoplasts of transformed mouse L cells (L929 cells, ATCC CCL 1) or Ehrlich ascites cells (ATC CL 77) according to described methods. In order to obtain complexes of permanently proliferating cells of other tissues or degree of differentiation as well cells of other species, it is also possible to use other tumor cell lines with the desired degree of differentiation and species as a source for isolating the complexes. When obtaining corresponding complexes from human cervix tumors, it is preferred to use the human cell lines HeLa, or from B-lymphoma lines and the B-cell lymphoma line BJAB. Moreover, it is also possible to use permanently growing cell lines that were immortalized as a consequence of an experimental immortalization, e.g. by fusion of primary cells with cytoplasts of permanently growing cells (EP-B-0 093 436, Abken et al., J. Cell. Biol. 130 (1986) 795–805) or by transfection with DNA from these cytoplasts (EP-B-0 256 512 and DE 42 18 945.4 and Abken et al., Proc. Natl. Acad. Sci. 85 (1988) 468–472).

Experience has shown that a cytoplasmic DNA fraction with a density of 1.86 g/cm³ prevails in Hodgkin lymphoma cells. This DNA is also linked to proteins. The DNA molecules contained in the fraction have a length between 50 and 500 bp. As is the case with cells from mouse tumors, all DNA molecules are linear. However, they do not hybridize with those of the mouse tumor cells. This demonstrates that both animal and human lymphoma cells in accordance with the invention contain cytoplasmic DNA sequences. The fraction in accordance with the invention can also be found in human tumor cells of colon and mamma carcinomas and human melanomas.

It is possible to isolate the proteins and/or the DNA from these complexes and to use these to detect human or animal cells having an unlimited proliferation and tumor-formation potential.

Another subject matter of the invention are, hence, proteins with a molecular weight of approx. 52, 62 and/or 64 kD which are suitable for the detection of human or animal cells having an unlimited proliferation or tumor-formation potential; they can be obtained by treating a complex of the invention with DNase I and isolating the released proteins of approx. 52, 62 and/or 64 kD and chromatographic or electrophoretic procedures.

In order to isolate these proteins, the complexes are treated with DNase I and the digested nucleic acids are separated from the proteins via gel filtration; the proteins are at the same time separated according to size. When using complexes from mouse L cells (L929) and/or Ehrlich ascites tumor cells, proteins with a size of 52, 62 and 64 kD are obtained. These proteins are characterized by their capability of binding the cloned pLC 108 DNA (SEQ ID NO 1) in accordance with the invention in the presence of 8 mM $Zn^{2+}$. The proteins from the Ehrlich ascites cells are characterized by their capability of binding cloned pEFC38 DNA (SEQ ID NO 29) in the presence of 8 mM $Na^+$. It is preferred to use a template-bound DNase for the preparation of these proteins, e.g. DNase that is covalently linked to sepharose.

Another subject matter of the invention are antibodies suitable for the detection of human or animal cells having an unlimited proliferation and tumor-formation potential; they can be obtained by immunization of animals with a complex or protein or DNA in accordance with the invention. It is possible to use any animal commonly used for immunization, including mice (e.g. MNRI or BALB/c strain) or rabbits and also immunization protocols (cf. e.g. J. Peters and H. Baumgarten, Monoklonale Antikörper, Springer Verlag, 2nd edition 1988).

The immunization of complexes in accordance with the invention, DNA and proteins generates antibodies that specifically bind to proteins from the cytoplasm cells having an unlimited proliferation or tumor-formation potential, but not to proteins from cells with normal proliferation capacities. The detection of these proteins with the aid of antibodies in accordance with the invention can be accomplished with the aid of methods such as ELISA, fluorescence methods, immunoassays, and competitive immunoassays all of which are known to the expert.

In addition to the protein portion of the complexes in accordance with the invention, the DNA portion can also be used for the detection.

Another subject matter of the invention is, hence, a DNA suitable for detecting human or animal cells having an unlimited proliferation or tumor-formation potential which can be obtained by means of cloning or enzymatic replication of the DNA of a complex in accordance with the invention.

Experience has surprisingly shown that the DNA of a complex of the invention can be ligated into cloning vectors like isolated DNA or can be enzymatically amplified, e.g. in a PCR, although in the complexes, this DNA is so tightly bound to the protein that it cannot be removed neither by means of detergents, proteases, high salt concentrations nor by means of thermal treatment. The DNA can be obtained by ligating the DNA of the complexes, e.g. in common vectors such as pUC19 and cloned in host organisms that are known to the expert such as E. coli HB101 or E. coli DH5α. Recombinant clones that contain the DNA sequence of the invention are then identified by hybridization with the complexes of the invention and the DNA is isolated. It was thus possible to obtain 20 recombinant plasmid clones from L929 cells (ATCC CCL 1) and 25 recombinant plasmid clones from Ehrlich ascites cells (ATCC CCL 77) which are suitable for the molecular identification of cells with an unlimited proliferation potential. These DNA sequences are listed in sequence protocols SEQ ID NO 1–45. With the aid of the sequences it is possible to detect other suitable DNA sequences of other cells of different differentiation degrees or other species in order to identify corresponding cells with an unlimited proliferation potential.

The DNA sequences shown in SEQ ID NO 1 and SEQ ID NO 29 are suitable for immortalization of human or animal cells (cf. German patent application P 42 18 945.4). All other DNA sequences (SEQ ID NO 2–28 and SEQ ID NO 30–45) have no immortalizing effect, but are suitable for detecting human or animal cells having an unlimited proliferation or tumor-formation potential.

A preferred subject of the invention is, hence, a DNA in accordance with the invention which contains one of the DNA sequences shown in SEQ ID NO 2–28 or SEQ ID NO 30–45 or hybridizes with one of these sequences.

Another preferred subject matter of the invention are DNA which contain one of the DNA sequences shown in SEQ ID NO 46–61 or hybridize with one or several of these sequences. The nucleic acid SEQ ID NO 46–58 are derived from DNA of HD 428 Hodgkin cells. The sequences of SEQ ID NO 59–61 are derived from DNA clones of MCF 7 cells (mamma carcinoma).

The nucleic acids of the invention can be DNA, but also RNA or nucleic acid analogs, e.g. those where the sugar phosphate back bone has been replaced by a polypeptide chain. The nucleic acid can be double-stranded, preferably, however, it is single-stranded. The invention also addresses each of the complementary sequences. In a preferred manner, the nucleic acids of the invention contain a sequence of at least 15 amino acids whereby the sequences are selected from a group of at least 15 amino acids taken from a sequence contained in a sequence according to SEQ ID NO 2–28 or 30–61,
  a sequence that is obtained by linking two sequences of SEQ ID NO 1–45, 46–58, or 59–61,
  sequences which code for the same amino acid sequence as the above listed two types,
  sequences which contain, within the specific sequence, at least 70%, preferably more than 90%, particularly preferred more than 95% of sequences that are specific to the above listed two types.

The nucleic acids have a particularly preferred length between 16 and 100 nucleotides. Depending on the length they can be obtained with the aid of molecular biological or chemical/synthetic methods.

Experience has surprisingly shown that most of the so far tested DNA sequences contain the consensus sequence NNAAANTNTNGAANTGTANNANTGNAA (SEQ ID NO 62).

Another subject matter of the invention is a method for obtaining the DNA in accordance with the invention by isolating a complex in accordance with the invention of human or animal cells that are capable of permanently dividing followed by cloning the DNA from this complex or replicating it enzymatically.

Another preferred subject matter of the invention is a method for obtaining a DNA in accordance with the invention where the DNA sequences in accordance with the invention are identified by hybridization of a genomic gene bank or a cDNA bank of human and animal cells with one of the DNA sequences shown in SEQ ID NO 1–61 and then isolating the hybridizing cloned DNA from the gene bank according to known methods. It is possible to use gene banks of permanently proliferating tumor cells and of normal cells or tissues.

Yet another preferred subject matter of the invention is a method for obtaining a DNA in accordance with the invention by binding the DNA of human and animal cells to a protein in accordance with the invention; the proteins are bound on nitrocellulose or other carrier membranes and incubated (e.g. for 4° C. for 30 min) in the presence of $Zn^{2+}$ or $Na^+$. Subsequently, the mixture is stringently washed at a high salt concentration (e.g. 0.1% SDS, 2×SSC).

Another preferred subject matter of the invention is a method for obtaining a DNA in accordance with the invention by enzymatically replicating a DNA or RNA fraction of human or animal cells; the starter molecules used are oligonucleotide molecules which hybridize with one of the sequences shown in SEQ ID NO 1–61. Preferred oligonucleotide starter molecules are those with a length between 20 and 30 base pairs. Enzymatic replication of the desired DNA sequences with the aid of polymerase chain reaction (PCR) is carried out according to methods that are known to the expert (Mullis and Fallona, Meth. Enzymol. 155 (1987) 335–350, Saiki et al., Science 239 (1988) 487–491). It is possible to use both gene banks as well as DNA or RNA preparations or cell lysates of permanently proliferating or normal senescent cells of humans or animals as DNA fractions.

Another variant of the method in accordance with the invention is the chemical synthesis of DNA in accordance with the invention containing one of the DNA sequences shown in SEQ ID NO 1–61 or parts of this DNA sequence. The synthesis is carried out according to oligonucleotide synthesis methods that are commonly used by the expert (F.

Eckstein, ed., Oligonucleotides and analogues: A practical approach, IRL Press at Oxford University press, Oxford (1991)); it is preferred to use commercially available oligo-nucleotide synthesis instruments.

Another subject matter of the invention is a method for the detection of human or animal cells having an unlimited proliferation or tumor-formation potential by detecting a complex in accordance with the invention in a mitochondria-free fraction of the cytoplasm of the cell to be examined. Normal cells with limited proliferation capacities do not contain such complexes in this fraction of the cytoplasm while cells with unlimited proliferation, e.g. tumor cells, contain several hundred copies of these complexes.

The complexes in accordance with the invention are excreted. The DNA-protein-link of these complexes is very stable against proteolytic digestion. The complexes can be detected in cell supernatants over a period of several weeks.

The complexes can also be contained in peripheral blood, in urine, or in other body fluids where they can be detected.

A preferred subject matter of the invention is, hence, a method for the detection of human or animal cells with unlimited proliferation or tumor-formation potential by detecting a complex in accordance with the invention in body fluids.

The complexes can be determined via their DNA contents or via gel electrophoresis while the complexes in accordance with the invention are carried along as standards for the determination of a positive reaction. In these methods, however, it is not possible to distinguish between complexes of different species or tissue types. Such a specific detection is, however, possible with the aid of the antibodies in accordance with the invention.

In addition to complete antibodies, it is also possible to use antibody fragments which contain the specific antigen recognition regions of the light and heavy chains ($V_L$ and $V_H$). These fragments can be coupled to carriers such as proteins, sugars or sepharose, or can be linked to dyes to generate fusion products.

Such a fusion product is preferably obtained by fusing the coding gene sequences for the antigen recognition regions $V_L$ and $V_H$ of the antibody to the gene sequences for a carrier molecule such as a surface protein of a phage or a capsid protein of a virus; this hybrid gene is then expressed in vitro. The method for isolating and cloning the gene sequences coding for the V regions of the antibody and their insertion into the DNA of other genes, e.g. in the gene sequence for the g3p phage protein and methods for expressing such a fusion protein are known to the expert (Orlandi et al., Proc. Natl. Acad. Sci. USA 86 (1989): 3833–3837; Chiang et al., BioTechniques 7 (1989): 360–366; Winter, G., and Milstein, C., Nature 349 (1991): 293–299). The fusion products (on the surface of phages or viruses or in isolated form) can then be used like an antibody in the detection of the complexes.

Finally, the complexes in the cells to be examined can also be detected by hybridization of a DNA fraction of these cells with a DNA in accordance with the invention. The advantage of this method is that it is possible to distinguish with these DNA probes between cells of different differentiation degrees (fibroma and/or ascites tumor) and species (mouse or human).

Another subject matter of the invention is, hence, a method for the detection of human or animal cells having an unlimited proliferation or tumor-formation potential by hybridization of a DNA fraction of these cells with a DNA of the invention.

A cytoplasmic cell fraction which contains the complexes of the invention can be used as DNA fraction. It is, however, also possible to use nuclear, chromosomal DNA of the cells to be examined. Experience has shown that, as compared to cells with the capability of unlimited proliferation, nuclear chromosomal DNA of normal transient proliferating cells has, after restriction digestion and analysis of the restriction fragments in a southern blot, another pattern of hybridizing restriction fragments when hybridizing a DNA sequence in accordance with the invention. Usually, additional restriction fragments which hybridize with the probes indicate the presence of cells having an unlimited proliferation and tumor-formation potential.

The DNA sequences in accordance with the invention exhibit such a high sensitivity and specificity that these samples can also be used for hybridization with cells or tissue in situ. Only those cells are labeled in the cytoplasm that exhibit unlimited proliferation or tumor-formation potential. For this in situ hybridization it is possible to use both cells that can be cultured in vitro and cells obtained in biopsies or tissue sections of biopsies without requiring a cultivation step in order to replicate the cellular material.

Another preferred subject matter of the invention is, hence, a variant of the method of the invention where the hybridization is carried out as an in situ hybridization.

The sensitivity of the method is further increased by replicating the DNA of the complexes from the cells to be examined in the detection reaction enzymatically, especially with the aid of polymerase chain reaction according to methods that are known to the expert (Mullis and Fallona, Meth. Enzymol. 155 (1987): 335–350; Saiki et al., Science 239 (1988), 487–491).

A preferred subject matter of the invention is, hence, a special embodiment of the method of the invention where a nucleic acid is enzymatically replicated from a lysate of the cells to be examined or a DNA or RNA fraction of these cells with the aid of oligonucleotides which hybridize with a DNA of the invention.

Such an amplification is possible although the DNA protein binding is stable with respect to high temperatures (1 hour at 90° C.), high salt concentrations (e.g. 6.9 mol/l cesium chloride) and with respect to proteinase K digestion (100 µg/ml for 1 hour at 60° C.).

The described method for detecting cells having an unlimited proliferation or tumor-formation potential is used for the detection of malignantant tumors where the cells of a biopsy, a tissue section, or cells or excreted complexes from body fluids of humans and animals are used as sample materials. The described method is, hence, suitable for detecting these cells. Moreover, when correspondingly modified, the described methods can also be used to isolate these cells. In this procedure, the described method is used particularly for identifying the desired cells in a certain fraction during the isolation procedure. It is possible to use antibodies in accordance with the invention and subsequently isolate the cells by means of fluorescence activated sorting (FACS).

The following examples explain the invention in greater detail in combination with the sequence protocols which show particularly preferred DNA sequences.

DETAIL DESCRIPTION OF THE INVENTION

EXAMPLE 1

Isolating Complexes and Cloning the DNA of these Complexes and Cloning the DNA of these Complexes Which are Suitable for Detecting Cells Having an Unlimited Proliferation or Tumor-formation Potential Cytoplasmic complexes are isolated from L929 mouse tumor fibroblasts (L929 cells, ATCC CCL 1) and Ehrlich ascites cells (EAZ, ATCC CCL 77). First, cytoplasts of these cells are obtained according to known methods (Wigler and Weistein, Biochem. Biophys. Res. Comm. 63 (1975) 669–674) with the aid of cytochalasine B (50 µg/ml), and then lysed by means of repeated freezing and thawing. The mitochondria are separated from the cytoplast lysate with the aid of a sucrose gradient according to J. Biol. Chem. 249 (1974) 7991–7995. The fractions which do not contain mitochondria are incubated for 30 min at 37° C. with RNase A (20 µg/ml) and RNase T1 (1000 U/ml) and subsequently with proteinase K (50 µg/ml) for 20–60 min at 60° C. From this mixture, the complexes are isolated according to known methods of DNA isolation, e.g. extraction with phenol or chloroform/isoamyl alcohol; a fraction which has a density of approx. 1.82–1.89 g/cm$^3$ in a cesium chloride gradient is enriched via a CsCl density gradient (Sambrook et al., Molecular Cloning, Cold Spring Harbor Laboratory, 2nd edition 1989). The fractions are dialyzed against 10 mmol/l Tris-HCl pH 7.2, 1 mmol/l EDTA and the complexes are precipitated with ethanol and sodium acetate.

In order to isolate the DNA of these complexes, the complexes are dialyzed against 10 mmol/l Tris-HCl, 1 mmol/l EDTA, pH 7.2. The DNA is then subject to a "filling reaction" with the aid of the Klenow DNA polymerase in the presence of dNTPs according to methods that are known to the experts (Sambrook et al., Molecular Cloning, Cold Spring Harbor, 2nd edition 1989); subsequently they are ligated into to pUC19 vector in the presence of 0–10 U ligase, and the resulting recombinant plasmid is cloned in *E. coli*. During the replication of the plasmids in the bacteria, protein-free copies of this recombinant DNA molecule are produced.

It is thus possible to obtain several independent plasmid clones of cytoplasmic complexes of L929 cells (pLC) and several plasmid clones from the corresponding fractions of Ehrlich ascites cells (pEFC) which are suitable for the detection of neoplastically transformed cells with an unlimited proliferation potential (see example 2). The corresponding DNA sequences are shown in SEQ ID NO 1–46.

EXAMPLE 2

Simplified Method for Isolating Complexes

Cells of the mouse tumor cytoplast line L929 (ATCC CCL 1) were lysed in the presence of 50 mmol/l Tris-HCl pH 7.2, 10 mmol/l EDTA, and 1.5 mmol/l magnesium chloride by repeated freezing and thawing; the nuclei were subsequently separated by 30 min of centrifugation at 6000 g. The so obtained supernatant was incubated for 20 min at 60° C. with proteinase K (100 µg/ml), and subsequently placed on a cesium chloride two-step gradient; the lower fraction (1 ml) had a density of approx. 1.80 g/cm$^3$ while the upper fraction (1 ml) had a density of approx. 1.70 g/cm$^3$. After centrifugation for 10 h at 150,000 g, the sediment is resuspended in 100 µl of 10 mmol/l Tris-HCl pH 7.2, 1 mmol/l EDTA, and the amount of resulting DNA is determined in this fraction as described in Example 1.

EXAMPLE 3

Detection of Human or Animal Cells with the Capability of Unlimited Proliferation Using Cytoplasmic Complexes The determination of cytoplasmic complexes in a lysate of these cells is used to detect human or animal cells having an unlimited proliferation or tumor-formation potential. First, the cytoplasts of these cells are obtained according to known methods (Wigler and Weistein, Biochem. Biophys. Res. Comm. 63 (1975) 669–674) using cytochalasin B (50 µg/ml) and lysed by repeated freezing and thawing. The mitochondria are separated from the cytoplast lysate with the aid of a sucrose gradient (J. Biol. Chem. 249 (1974) 7991–7995), and the mitochondria-free fractions are incubated with RNase A (20 µg/ml) and RNase T1 (1000 U/ml) and subsequently with proteinase K (50 µg/ml). The mixture is then subject to ultra-centrifugation in a CsCl density gradient according to known methods (Sambrook et al., Molecular Cloning, Cold Spring Harbor Laboratory, 2nd edition 1989). Possibly present complexes are determined via the DNA contents of the fraction with a density of approx. 1.82–1.89 g/cm$^3$ (results see Table 1). The DNA contents is determined photometrically or by taking up ethidium bromide according to known methods (Sambrook et al.).

Experience has shown that normal mouse embryo fibroblasts (MEF) which have a limited life expectancy and pass only through a given number of cell divisions in a culture (approx. 15–20 passages) have no detectable DNA in these fractions of the cytoplasm. Human lymphocytes from peripheral blood (PBL) which undergo in this differentiation stage only 3–5 cell divisions in vivo and in vitro before they are subject to programmed cell death, have no detectable cytoplasmic complexes either. Cells with unlimited proliferation capacity such as cells of established lines of malignantant tumors, however, do contain cytoplasmic complexes in the corresponding fractions (Table 1).

TABLE 1

Detection of human or animal cells with the capability of unlimited proliferation using the determination of cytoplasmic DNA protein complexes

| Cells | Species | Cell phenotype | Proliferation | Cytoplasmic DNA protein complex (µg DNA/10$^9$ cells) |
|---|---|---|---|---|
| PBL | human | normal | transient | <1 ng |
| WIL-2 | human | tumor cells | unlimited | ca. 200 ng |
| HS-Sultan | human | tumor cells | unlimited | ca. 100 ng |
| MEF | mouse | normal | transient | <1 ng |
| L929 | mouse | tumor cells | unlimited | ca. 200 ng |
| EAZ | mouse | tumor cells | unlimited | ca. 500 ng |
| Ag8.653 | mouse | tumor cells | unlimited | ca. 300 ng |

PBL: Human lymphocytes from peripheral blood
WIL-2: Human T-leukemia line (ATCC CRL 8062)
HS-Sultan: Human leukemia line (ATCC CRL 1484)
MEF: Mouse embroy fibroblasts
L929: Neoplastically transformed line of mouse L cells (ATCC CCL 1)
EAZ: Neoplastically transformed line of the mouse ascites tumor (ATCC CCL 77)
Ag8.653: Mouse myeloma line (ATCC CRL 1580)

EXAMPLE 4

Detection of Human or Animal Cells Having an Unlimited Proliferation or Tumor-formation Potential in a Cell Lysate by Hybridizing Cytoplasmic Complexes with the pLC108 DNA Probe (SEQ ID NO 1)

Cells of neoplastically transformed mouse line L929 (A) and primary mouse embryo fibroblasts (MEF) (passage 5) (B) are lysed in the presence of 50 mmol/l Tris-HCl, pH 7.2, 10 mmol/EDTA, 3 mmol/l MgCl$_2$ by repeated freezing and thawing. The nucleic are sedimented by means of centrifugation at 6000 g for 20 min. The supernatant (cytoplasm lysate) is incubated with proteinase K (50 μg/ml) for one hour at 60° C. Subsequently, KCl (0.5 mol/l) is added to the fraction and filtered in a dilution series with the aid of a BA85 nitrocellulose filter (manufactured by Schleicher & Schuell) using a "MINIFOLD" instrument. Since the DNA protein binding of the complexes to be detected is stable with respect to the high salt concentration, and since the proteins in the complexes are not digested by the proteinases, the complexes (as opposed to other DNA protein associations) remain intact under the selected conditions and are retained in the filter. The nitrocellulose filter is then washed twice with 20×SSC and dried at 120° C. for 15 min. To detect the complexes of mouse fibroblasts with the capability of unlimited proliferation, hybridization with $^{32}$P-labeled DNA of the sequence shown in SEQ ID NO 1 (pLC108) according to known methods under stringent hybridization conditions (55% formamide, 1 mol/l NaCl, 1% SES, 10% dextran sulfate, 100 μg/ml Herring Sperm DNA) at 42° C. (Sambrook et al., Molecular Cloning, Cold Spring harbor Laboratory, 2nd edition, 1989).

Result:

(A) The samples of the cytoplasmic lysates of L929 cells show in dependency upon the dilution of the lysate a hybridization signal with the probe of the sequence shown in SEQ ID NO 1 (LC108).

(B) There is no hybridization with the cytoplasmic lysate of the primary mouse fibroblasts (MEF).

EXAMPLE 5

Detection of Human and Animal Cells Having an Unlimited Proliferation or Tumor-formation Potential with the Aid of in Situ Hybridization L929 mouse tumor cells (ATCC CCL 1) (A) and primary mouse embryo fibroblasts (passage 5) (B) are cultured on DMEM medium on microscopic slides. Both cultures contain proliferating cells; the L929 cells have an unlimited proliferation potential while primary mouse fibroblasts stop proliferation after approx. 15–20 passages in the culture and then die. Moreover, a tumor is induced in C3H mice by subcutaneous injection of L929 cells; then, a frozen section of this tumor is obtained and placed on a microscopic slide (C). The microscopic slide is washed twice briefly with PBS (Dulbecco/Vogt, J. Exp. Med. 99 (1954), 167–182) and coated with 200 μl neutral paraform aldehyde solution (5%) in order to fix it; subsequently it is washed twice in ethanol (70%). In order to detect cells with unlimited proliferation potential, the oligonucleotide (primer A): 5'GATCT-TGAGTTTCCTCGTTGTAGGT3' (SEQ ID NO 63) (corresponding to nucleotides 1–25 of SEQ ID NO 1) is used which is analogous to the sequence (pLC108) shown in SEQ ID NO 1. This oligonucleotide (100 pmol) is labeled with 25 U of terminal transferase (Boehringer Mannheim GmbH, Cat. No. 220582) for 20 min at 37° C. with digoxigenin-labeled dideoxy UTP (DIG-11-ddUTP) (1 nmol) in 20 μl of the reaction buffer (20 mmol/l potassium cacodylate, 25 mmol/l Tris-HCl, pH 6.8, 5 mmol/l $CoCl_2$, 0.25 mg/ml bovine serum albumin). The labeled oligonucleotide is then separated from the free DIG-ddUTP nucleotides by gel filtration over a P10 column (manufactured by Biorad). For hybridization, the microscopic slides with the fixed cells or tissue sections are coated with 200 μl hybridization solution (50% deionized formamide, 4×SSC, 10% dextran sulfate, 1×Denhardt's solution, 0.25 mg/ml denatured tRNA, 0.5 mg/ml denatured hering sperm DNA). The solution on the slides is then covered with covering glasses and the microscopic slide is incubated for one hour at 42° C. in a humid chamber. Subsequently, the solution is removed again, the cells are coated with DIG-ddUTP-labelled oligonucleotide (5 ng DNA in 40 μl hybridization solution) and incubated in a humid chamber overnight at 42° C. Subsequently, the microscopic slides are washed twice for 20 min in 2×SSC at 42° C. In order to detect the hybridized oligonucleotides, the cells are incubated for 20 min at room temperature with an FITC-coupled anti-DIG antibody (manufactured by Boehringer Mannheim, Cat. No. 1207741). Non-bound antibodies are removed by washing twice in PBS. The preparations are then evaluated with the aid of a fluorescence microscope at a wavelength of 470 nm.

Results:

(A) L929 tumor cells show increased fluorescence in cytoplasm while the nucleic acid do not show any fluorescence. An accumulation of hybridization signals in the vicinity of the nucleic acid of the cytoplasm is particularly significant. In control experiments ("fake hybridization" of the cells without oligonucleotide, but incubation with an FITC anti-DIG antibody) there is no fluorescence signal generated.

(B) After hybridization of primary mouse embryo fibroblasts (MEF) the cells are not labeled (neither in the cytoplasm nor in the nucleus).

(C) After hybridization of the tissue section of a tumor induced by L929 cells, the tumor cells show a fluorescence in cytoplasm while the surrounding (normal) tissue and subcutaneous tissue do not show any hybridization signals. In control experiments ("fake hybridization") of the cells without oligonucleotide, but incubation with the FITC anti-DIG antibody) there is no fluorescence signal generated. The cytoplasmic complexes of the tumorigenic L929 cells with unlimited proliferation potential can also be detected by hybridization with an oligonucleotide sample of the invention in a tissue section. It is thus possible to identify also neoplastically transformed cells in a tissue section or in a biopsy.

EXAMPLE 6

Detection of Human or Animal Cells Having an Unlimited Proliferation or Tumor-formation Potential by Hybridization of Chromosomal DNA Chromosomal DNA is isolated from cells of the mouse lines of neoplastically transformed L929 fibroblasts (ATCC CCL 1), Ehrlich ascites tumor cells (ATCC CCL 77), myeloma Ag8.653 cells (ATCC CRL 1580), WEHI164 fibrosarcoma cells (ATCC CRL 1751) of permanently proliferating, but non-tumorigenic fibroblast lines NIH3T3 (ATCC CRL 6473) and from primary mouse embryo fibroblasts (MEF) (passage 6) obtained according to known methods by incubating cut-up mouse embryos (type 12) with collagenase (0.1 U/ml) and dispase (0.8 U/ml) in PBS for 1 h at 73° C. (Abken et al., J. Cell Biol. 103 (1986), 795–805; Sambrook et al., Molecular Cloning, Cold Spring Harbor Laboratory, 2nd edition 1989). After cleavage of the DNA with Hind III, the DNA is electrophoretically separated and transferred onto a nylon membrane in a southern blot. After detection of cells with unlimited proliferation, the blood is hybridized with a $^{32}$P-labeled DNA of the sequence shown in SEQ ID NO 29 (pEFC38).

Result:

There are varying sizes of the hybridizing restriction fragments in the cells examined (Table 2). The following characteristics could be identified:

1. Cells with limited life expectancy and proliferation (e.g. MEF) show a Hind III lane of approx. 3 kb and of approx. 2.6 kb.

2. Cells with unlimited proliferation potential and tumor formation (L929, EAZ, Ag8.653, WEHI164) or unlimited proliferation without tumor formation (NIH3T3) show additional hybridization signals of Hind III restriction fragments with certain sizes. The 3 kb lane is frequently missing. What is common to all unlimited proliferating cells is the occurrence of certain additional Hind III restriction fragments of the following sizes: 10 kb, 13 kb, 14.5 kb, 16.6 kb, and 21.1 kb. The occurrence of these additional hybridizing lanes and/or the missing of the hybridizing 3 kb Hind III lanes when the DNA probe shown in SEQ ID NO 29 (EFC38) is used, shows mouse cells with unlimited proliferation potential.

TABLE 2

Detection of human or animal cells having an unlimited proliferation or tumor-formation potential by hybridizing chromosomal DNA with the pEFC38 DNA sample (SEQ ID NO 29)

| Cells | Hybridizing restriction fragments (kb) | | | | |
|---|---|---|---|---|---|
| | 1.9 kb | 2.6 kb | 3.0 kb | 6.0 kb | >10 kb |
| MEF | − | + | + | − | − |
| NIH 3T3 | − | + | + | − | + |
| L929 | + | + | + | + | + |
| EAZ | − | + | + | + | + |
| Ag8.653 | + | + | − | − | + |
| WEHI164 | − | + | − | − | + |

+/− Hybridization/no hybridization with a Hind III restriction fragment of genomic DNA of the sizes listed. Hind III restriction fragments >10 kb: 10 kb, 13 kb, 14.5 kb, 16.6 kb, 21.1 kb

EXAMPLE 7

Detection of Human or Animal Cells with the Capability of Unlimited Proliferation by Amplifying the DNA of Certain Cytoplasmic DNA Protein Complexes The permanently proliferating L929 mouse fibroma cells carry cytoplasmic DNA protein complexes which contain a DNA that hybridizes with the LC108 DNA (SEQ ID NO 1). The mouse tumor cells of other differentiation degrees like Ehrlich ascites tumor cells, have, however, complexes which contain a DNA that hybridizes with the EFC 38 DNA (SEQ ID NO 29), but not with the LC108 DNA or any other of the sequences given in SEQ ID NO 1–20. As opposed to the tumor cells L929 and the Ehrlich ascites cells with unlimited proliferation, it is not possible to detect such complexes in the cytoplasm of primary fibroblasts with limited proliferation capacity such as mouse embryo fibroblasts. With the aid of a polymerase chain reaction, it is possible to specifically amplify the DNA of the respective complexes to thus detect the presence of permanently proliferating cells in the cell mixture. Under the selected conditions of the experiment, it is also possible to distinguish between the degree of differentiation of these cells to identify either fibroma or ascites cells.

Portions of $10^4$ cells of primary mouse embryo fibroblasts (passage 6), neoplastically transformed mouse cells of the lines L929 (ATCC CL 1) and Ehrlich ascites (ATC CCL 77) or a mixture of these cells are resuspended in 5 µl of PBS; then 15 µl of $H_2O$ are added and the mixture is immediately frozen at −20° C. and then heated up to 95° C. for 10 min. The samples are then incubated in the presence of proteinase K (500 µg/ml) for 1 h at 55° C. and subsequently again heated up for 10 min at 95° C. The following reaction mixture is added to amplify the DNA of cytoplasmic DNA protein complexes using PCR technology according to known methods (Mullis and Fallona, Meth. Enzymol. 155 (1987): 335–350; Saiki et al., Science 239 (1988): 487–491):

3 µl 10×Taq buffer (200 mmol/l Tris-HCl, pH 8.4, 250 mmol/l KCl, 0.5% Tween 20, 1 mg/ml BSA);

0. 5 µl 100 mmol/l $MgCl_2$;

1 µl dNTP solution (2 mmol/l dATP, 2 mmol/l dCTP, 2 mmol/l dGTP, 2 mmol/l dTTP);

1 U Taq polymerase (Boehringer Mannheim);

portions of 100 ng of primer oligonucleotides A and B for the amplification of the LC108 homologous DNA and/or the primer oligonucleotides C and D for the amplification of the EFC38 homologous DNA of cytoplasmic DNA protein complexes.

The primer oligonucleotide sequences (primer) are partial sequences of the DNA sequences shown in SEQ ID NO 1 and SEQ ID NO 29.

Primer A: 5'GATCTTGAGTTTCCTCGTTGTAGGT3' (SEQ ID NO 63)

(nucleotide 1–25 of SEQ ID NO 1).

Primer B: 5'GATCCAAAGCCCTCTGCTGGCCTCC3' (SEQ ID NO 64)

(complementary to the nucleotides 203–179 of SEQ ID NO 1)

Primer C: 5'GATCCAATCAGCTCAGCCACCCCCA3' (SEQ ID NO 65)

(nucleotides 1–25 of SEQ ID NO 29)

Primer d: 5'AAAACCAGGCCCTCCCACATG3' (SEQ ID NO 66)

(complementary to the nucleotides 372–352 of SEQ ID NO 2)

30 cycles with the following temperature profile are then carried out:

1. 1×[2 min 95° C.]

2. 30×[30 sec 55° C.; 90 sec 72° C.; 60 sec 95° C.]

3. 1×[15 min 72° C.]

The so amplified DNA of cytoplasmic complexes is electrophoretically separated in agarose gel (1%) and after incubation with ethidium bromide made visible in UV light.

Result:

The amplification of the DNA of the LC108 homologous complexes with the aid of primers A and B, generates an amplified DNA (203 bp) when the permanently proliferating L929 cells are used, but not when MEF or Ehrlich ascites cells are used. Amplification of the EFC38 homologous DNA generates an amplified DNA (372 bp) in the lysate of Ehrlich ascites cells, but not in the samples of the MEF of L929 cells (Table 3). The reaction mixture of L929 cells or Ehrlich ascites cells in $10^4$ mouse embryo fibroblasts (MEF) shows that it is possible to detect with this experiment setting cells with unlimited proliferation potential (L929, EAZ) in $10^4$ normal mouse fibroblasts with limited proliferation potential. When selecting the primer pairs (A, B or C, D) it is also possible to determine the degree of differentiation of these malignant cells in the cell mixture (fibroma [L929] or ascites [EAZ] cells).

TABLE 3

Detection of human or animal cells with the capability of unlimited proliferation by amplifying the DNA of certain cytoplasmic complexes

| Cell/Cell mixture | | Number of cells | | PCR amplification with the aid of | |
|---|---|---|---|---|---|
| (a) | (b) | (a) | (b) | Primer A, B | Primer C, D |
| MEF | — | $10^4$ | — | — | — |
| L929 | — | $10^4$ | — | + | — |
| EAZ | — | $10^4$ | — | — | + |
| MEF | L929 | $10^4$ | 1 | + | — |
| MEF | EAZ | $10^4$ | 1 | — | + |

+/− Amplification/no amplification of the DNA of cytoplasmic complexes

EXAMPLE 8

Detection of the Number of Human or Animal Cells with the Capability of Unlimited Proliferation in a Cell Mixture by Means of Competitive PCR Amplification of the DNA of Cytoplasmic Complexes With the aid of the experimental arrangement given here, it is possible to (approximately) determine the number of cells with unlimited proliferation and a certain degree of differentiation in a mixture of normal pre-senescent cells with limited proliferation potential. The DNA of cytoplasmic complexes is amplified in a PCR reaction using specific primer oligonucleotides; the specific DNA (to be detected) competes with a constant quantity of known, competing DNA. Owing to the fact that the PCR reaction is carried out in the presence of DIG-dUTP, the amplified DNA is labeled with modified nucleotides. The amplified DNA of the complexes that is to be detected is then bound by hybridization to a single-stranded homologous capture probe and the quantity of the bound DIG-labeled DNA is determined with the aid of an anti-DIG ELISA test. The method is designed such that the experimental steps can be carried out on a microtiter plate prepared for this purpose.

1. Preparation of the Cell Lysate

Cell mixtures (total of $10^5$ cells) of primary mouse embryo fibroblasts (MEF) and Ehrlich ascites cells (EAZ) which contain the Ehrlich ascites cells to be detected in increasing concentrations are taken up in 100 µl 50 mmol/l Tris-HCl, pH 7.2, 10 mmol/l EDTA, 3 mmol/l $MgCl_2$, and the cells are lysed by repeated freezing and thawing. The nuclei are sedimented by centrifugation for 10 min at 6000 g; proteinase K (50 µg/ml) is added to the supernatant and incubated for 1 h at 55° C. Subsequently, the proteinase is inactivated by heating up to 95° C. for 10 min.

2. Preparation of a Specific Capture Probe

A capture probe RNA which contains a partial sequence of the sequence (372 bp) shown in SEQ ID NO 29 is used for the detection of Ehrlich ascites cells. The DNA sequence (from base pair 26 to base pair 350 of the sequence shown in SEQ ID NO 29) is cloned in an SP6 vector, e.g. pSPT18 according to known methods (Sambrook et al., Molecular Cloning, Cold Spring Harbor Laboratory, 2nd edition, 1989). Using an SP6-RNA polymerase, a single-stranded RNA sample is prepared and purified according to known methods (Dunn and Studier, J. Mol. Biol. 166: 477, 1983; Kassavetis et al., J. Biol. Chem. 257: 5779, 1982), preferably with the aid of a template-bound DNase I (free of RNase). The RNA is labeled at its terminus with the aid of a biotin UTP and RNA ligase and non-incorporated biotin UTP is removed by means of gel filtration on a SEPHADEX G50 column (Biorad). The biotin EFC38(28–346) capture probe is now available for binding to a streptavidin-coated microtiter plate.

3. Coating of the Microtiter Plate

The bottom of a 96-well microtiter plate suitable for ELISA tests is coated with streptavidin, washed, and dried. Subsequently, the biotin-labeled capture probe [500 ng biotin EFC38(26–246)] is added to 100 µl TE buffer (10 mmol/l Tris-HCl, pH 7.5, 1 mmol/l EDTA) and incubated for 1 h at 37° C. On the microtiter plate, the capture probe binds to streptavidin via the biotin. Subsequently, the wells of the microtiter plate are washed several times with TE buffer.

4. Preparation of an EFC38-PCR Competition Probe

Competitive (quantitative) amplification using the PCR technology requires a DNA that competes with the DNA to be determined for the binding of the specific oligonucleotide primers. To accomplish this, a double-stranded competition DNA is prepared which has a length of 372 bp as does the DNA shown in SEQ ID NO 29; base pairs 1–25 and base pairs 351–372 are identical with the DNA shown in SEQ ID NO 29. Base pairs 26–350, however, are not identical with the DNA sequence shown in SEQ ID NO 29, but show a random DNA sequence that could be obtained with the aid of conventional oligonucleotide synthesis instruments.

5. Competitive PCR of the EFC38 homologous DNA of the DNA protein complexes

The following PCR reaction mixture is added to the cell lysate (100 µl) (from 1) to amplify the EFC38 homologous DNA to be determined:
   12 µl 10×Taq buffer (200 mmol/l Tris-HCl, pH 8.4, 250 mmol/l KCl, 0.5% TWEEN 20,
   1 mg/ml BSA);
   1.5 µl 100 mmol/l $MgCl_2$;
   2.5 Ml DIG-dNTP solution (2 mmol/l dCTP, 2 mmol/l dCTP, 2 mmol/l dGTP, 2 mmol/l dTTP, 0.7 mmol/l DIG-dUTP) (Boehringer Mannheim);
   2 U Taq polymerase (Boehringer Mannheim);
   100 ng each of primer oligonucleotides C and D (see Example 7)

30 cycles with the following temperature profile are carried out:
   1. 1×[5 min 95° C.]
   2. 30×[30 sex 55° C.; 90 sec 72° C.; 60 sec 95° C.]
   3. 1×[15 min 72° C.]

Subsequently, the samples are heated up for 10 min to 95° C., cooled down to 75° C., and then added to the preheated microtiter plate and slowly cooled down to room temperature (2° C. per min).

6. Quantitative Determination of the Amplified DNA

The wells of the microtiter plate are washed several times with portions of 500 µl of PBS and incubated for 1 h at 37° C. with an anti-DIG antibody, Fab fragments coupled with peroxidase (150 mU/ml in PBS, 0.5 mg/ml bovine serum albumin) (manufactured by Boehringer Mannheim). The wells are washed twice with PBS and then incubated for 1 h at room temperature with 200 µl ABTS substrate (peroxidase substrate solution). The absorbance is measured in the wells at a

EXAMPLE 9

Quantitative Detection of Complexes Excreted by Cells with an Unlimited Proliferation Potential Cells with unlimited proliferation potential excrete cytoplasmic complexes. The detection of these excreted complexes can, hence, be used for the detection of cells with the capability of unlimited proliferation, particularly for the detection of tumor cells. This example demonstrates that the excreted complexes of Ehrlich ascites cells can be measured in cell-free culture supernatant. This method allows the specific determination of certain complexes to distinguish tumor cells of varying differentiation degrees.

1. Preparation of the Cell-free Culture Supernatant

Ehrlich ascites cells and primary mouse embryo fibroblasts are cultured in Transwells™ plates (Costar, Cambridge, Mass.) which allow to grow the cells in a lower compartment while the culture supematant is separated from the cells by a membrane having pores (diameter 0.3 $\mu$m); the supernatant can then be gathered in an upper compartment. Excreted complexes diffuse into the cell-free upper compartment. Portions of $10^4$, $10^5$, and $10^6$ cells are placed in 3 ml of medium and after 2 days, the cell-free culture supernatant (100 $\mu$l) is obtained from the upper compartment. Proteinase K (50 $\mu$g/ml) is added to the supernatant and incubated for 1 h at 55° C. Subsequently, the probe is heated up for 10 min to 95° C. in order to inactivate the proteinase.

2. Preparation of the Microtiter Plates, the "capture probe" and the Competition DNA The procedure for coating the ELISA microtiter plate with streptavidine and preparing the biotinylated capture probe is already given in Example 8; the DNA sequences used are also the ones of Example 8. The competition DNA is also prepared as described in Example 8.

3. Competitive PCR Amplification of the DNA of the Complexes to be Determined

The culture supernatant is added to the coated microtiter wells and the PCR reaction mixture described in Example 8 is also added. The DNA is amplified in the presence of DIG-dUTP also as described for Example 8. Subsequently, the mixture is heated up for 10 min at 95° C. and slowly cooled down to room temperature (2° C./min).

4. Determination of the Amplified DNA

The wells of the microtiter plate are washed several times with portions of 500 $\mu$l PBS and incubated for 1 h at 37° C. with an anti-DIG antibody, Fab fragments, coupled with alkaline phosphatase (20 $\mu$g/ml in PBS, 0.5 mg/ml of bovine albumin) (manufactured by Boehringer Mannheim). The wells are then washed twice with 500 $\mu$l PBS each time. NADPH is added and reacted via the alkaline phosphatase of the bound anti-DIG antibody to give NADH. Using an enzymatic cycle (AMPAK®, Dako) which includes alcohol dehydrogenase and diaphorase, the NADH is now reacted via the enzyme diaphorase to give, after addition of INT, NAD$^+$ and formazane. After addition of ethanol, the alcohol dehydrogenase reacts the NAD$^+$ into acid aldehyde and NADH which in turn is available for reaction by the diaphorase enzyme. In each of these cycles, one molecule of formazane is produced. The absorbance of the so produced dye is measured at 492 nm using a microplate reader.

The competitive amplification of the DNA of the complexes to be determined using the PCR technology in the presence of DIG-dUTP and the detection of the amplified DNA using alkaline phosphatase-coupled anti-DIG antibodies as well as the subsequent amplification of the signal in an enzymatic cycle allows an extremely sensitive detection of the cellularly excreted complexes. The measured absorbance is proportional to the quantity of PCR amplified, DIG-labeled DNA from the excreted complexes and directly proportional to the quantity of Ehrlich ascites cells used in the diffusion chamber culture.

EXAMPLE 10

Isolation of the DNA Protein Complexes for the Detection of Hodgkin Lymphoma Cells Cells of the human Hodgkin lines HD 540 (L540) and HD 428 (L428) (Diehl et al., Cancer Treat. Rev. 66, 615–632 (1982) were deposited with the German collection of microorganisms and cell cultures (DSM) in Mascheroder Weg 1b, D-38124 Braunschweig on Jun. 29, 1994 under the number DSM ACC2177 (HD 540) or can be obtained from the public collection of the DSM under No. DSM ACC197 (L428). Said cells are lysed in the presence of 50 mmol/l Tris, pH 7.2, 10 mmol/l EDTA, and 1.5 mmol/l MgCl$_2$ by repeated freezing and thawing; nuclei are then separated by 30 min of centrifugation at 6000 g. The so obtained supernatant is incubated for 20 min at 60° C. with proteinase K (100 $\mu$g/ml) and subsequently placed on a cesium chloride two-step gradient; the lower fraction (1 ml) has a density of approx. 1.80 g/cm$^3$ while the upper fraction (1 ml) has a density of approx. 1.70 g/cm$^3$. After centrifugation for 10 h at 150,000 g, the sediment is resuspended in 100 $\mu$l 100 mmol/l Tris-HCl, pH 7.2, 1 mmol/l EDTA and dialyzed against 10 mmol/l Tris-HCl, 1 mmol/l EDTA, pH 7.2; the quantity of the so obtained DNA in this fraction is determined as described in Example 1.

The DNA is then subject to a "filling reaction" with the aid of the Klenow DNA polymerase in the presence of dNTPs according to methods that are known to the expert (Sambrook et al., Molecular Cloning, Cold Spring Harbor, 2nd edition, 1989) and then ligated into the pUC19 vector in the presence of 10 U of ligase; the resulting recombinant plasmid is cloned in *E. coli*. Protein-free copies of this recombinant DNA molecule are then produced in the bacteria during replication of the plasmid.

It is thus possible to obtain several independent plasmid clones of cytoplasmic complexes of human Hodgkin cells (pHD540, pHD420). The insert DNA of these plasmid clones is suitable for the detection of neoplastically transformed cells of the Hodgkin lymphoma when Examples 3–9 are applied correspondingly. The DNA sequences used are those shown in SEQ ID NO 45–85.

These sequences do not hybridize with the sequences found in the mouse cells.

EXAMPLE 11

Use of Polyclonal Rabbit Serum to Cytoplasmic DNA Protein Complexes to Detect Mouse Tumor Cells Mouse tumor cells are to be detected with a specific antiserum to cytoplasmic DNA protein complexes. To accomplish this, a protein lysate of these cells is prepared, electrophoretically separated and applied onto a carrier membrane and incubated with the specific antiserum from rabbit in a western blot. Bound rabbit antibodies are detected with a secondary anti-rabbit antibody and in a chemiluminescence reaction.

Procedure:

1. Obtaining the Anti-serum

The rabbits were immunized with DNA protein complexes (isolated from the cytoplasm of mouse L929 cells) by three s.c. injections in intervals of 3 weeks; the serum was subsequently obtained.

2. Obtaining a Protein Lysate

The L929 cells (mouse tumor cells) and MEF (mouse normal embryonic fibroblasts) were lysed in the presence of 50 mM Tris-HCl, pH 7.2, 10 mM EDTA, 3 mM $MgCl_2$, 0.3% NP40. Cellular fragments, nuclei and membranes were separated by centrifugation at 8000 g for 2 min. The supernatant (protein fraction) is stored by −20° C.

3. Western Blot and Detection Reaction

The protein fraction of the L929 cells and MEF (corresponding to approx. $10^5$ cells) as well as the isolated DNA protein complex (1 μg) (as positive controls) are denatured in the presence of SDS; they are then electrophoretically separated in an SDS polyacrylamide gel and electrophoretically transferred onto a nitrocellulose membrane according to a method known to the expert (E. Harlow, Antibodies, Cold Spring Harbor Laboratories, CSH Press). The membrane is incubated for 1 h in TBS (20 mM Tris, 137 mM NaCl, pH 7.6), 3% (V/V) Tween 20, 5% (w/v) dry milk powder; subsequently, the rabbit antiserum (1:5000) is added and the mixture is again incubated for 1 h. The membrane is washed in TBS, 3% Tween 20, then incubated in a goat anti-rabbit antibody (HRPO-labeled) (1:5000).

The mixture is washed again and the detection solution (ECL, Amersham, RPN 2106, 2108, 2109) is added and an autoradiography is carried out.

Result:

The antiserum from the protein lysate of the L929 tumor cells reacts with proteins of a molecular weight of approx. 36 kD, 52 kD, 62 kD, 64 kD and with protein aggregates of >150 kD. The proteins with a molecular weight of 52 kD, 62 kD, 64 kD are also found in the isolated DNA protein complexes from tumor cells (positive controls) by reaction with antiserum. The lane at 36 kD is most likely a protein digestion product.

In the protein lysate of the MEF normal cells there are no specific reactions with the antiserum. The slight reaction with protein aggregates of >150 kD is likely to be an unspecific binding of the antiserum.

EXAMPLE 12

Isolation of DNA Protein Complexes from Mamma Carcinoma

Corresponding to the procedure described in Example 10, DNA protein complexes are obtained from the MCF 7 cell line of the mamma carcinoma. A part of the nucleic acid is sequenced and contained in SEQ ID NOS 59–61. These sequences can be used as probes to identify and isolate mamma carcinoma cells which contain the complexes in accordance with the invention. After in vitro or in vivo replication of the nucleic acids, the entire sequence of this DNA of these complexes can be determined. The so far found sequences do not hybridize with the sequences found in Hodgkin or mouse cells. Another subject matter of the invention are also nucleic acids which are part of the entire sequence of the complexes and their functional equivalence are described as above.

As used in this application, complementary is defined as having at least 95% Watson-Crick base pairing.

ADDITIONAL EXAMPLES

EXAMPLE 13

Detection of Human or Animal Cells with the Capability of Unlimited Proliferation by Determining Cytoplasmic DNA Protein Complexes Using a Consensus Probe Like numerous other tumor cells, mouse Ehrlich ascites cells (ATCC CCL 77) and human L-428 Hodgkin lymphoma cells have the capability of permanently proliferating in vitro and forming tumors in vivo. As opposed to tumor cells, normal mouse embryo fibroblasts (MEF) have a limited life expectancy and undergo in culture only a limited number of cell divisions (approx. 15–20 passages. Human lymphocytes from peripheral blood (PBL) undergo in this stage of differentiation only approx. 3–5 cell divisions before they are subject to programmed cell death. The detection of cells with unlimited proliferation potential and the capability of forming tumors as described here is based on the fact that cytoplasmic DNA protein complexes isolated from Ehrlich ascites cells and their DNA sequences homologous to the consensus probe are detected by means of hybridization.

The cells are lysed in the presence of 50 mmol/l Tris-HCl, pH 7.2, 10 mmol EDTA and 1.5 mmol/l $MgCl_2$ by repeated freezing and thawing; the nuclei are then separated by centrifugation for 30 min at 6000 g. The so obtained supernatant is incubated for 20 min at 60° C. with proteinase K (100 μg/ml) and then subject to ultracentrifugation in a continuous CsCl gradient (initial density 1.70 g/cm$^3$) at 180,000 g, 10 h, and 10° C. The fractions of a density of approx. 1.82–1.89 g/cm$^3$ are dialyzed against 10 mmol/l Tris-HCl, pH 7.2 in 1 mmol/l EDTA. The DNA of the DNA protein complexes containing these fractions is denatured in the presence of 15×SSC by heating up to 100° C. for 2 min and then applied onto a nylon membrane using the dot blot method (Sambrook et al., Molecular cloning, Cold Spring Harbor, 2nd edition, 1989). A consensus probe was prepared using an oligonucleotide synthesis instrument (manufactured by Applied Biosystems); random incorporation of bases A, T, G or C occurred at the N positions of SEQ ID NO 62. After the synthesis, the DNA molecules (100 pmol) of the oligonucleotide mixture were labeled with DIG-ddUTP (1 nmol) (Boehringer Mannheim) using terminal transferase (25 U) (Boehringer Mannheim) in the presence of 20 μl labeling buffer (20 mM potassium cacodylate, 25 mM Tris-HCl, 5 mM $CoCl_2$, 0.25 mg/ml bovine serum albumin pH 6.8) for 20 min at 37° C. The labeled oligonucleotides were separated from non-incorporated DIG-ddUTP by means of chromatography on a P10 column (Biorad). The DNA of the DNA protein complexes were hybridized with the DIG-labeled consensus DNA probe (SEQ ID NO 62) according to methods known to the expert (Sambrook et al., 1989) in the presence of a solution of 10% dextran sulfate, 55% deionized formamide, 1% SDS, 1 mol/l NaCl, 100 μg/ml of herring sperm DNA at 42° C. Subsequently, the bound DNA probe is detected at 37° C. using an anti-DIG antibody (Fab fragments) coupled to alkaline phosphatase (150 mU/ml in PBS, 0.5 mg/ml bovine serum albumin) (Boehringer Mannheim). The membrane is washed twice in PBS, incubated with CSPD (AP substrate solution) for 15 min at 37° C. for chemiluminescence and exposed on an x-ray film. The blackening of the film is measured with the aid of a densitometer. The blackening of the film is proportional to the quantity of bound consensus DNA probe and, hence, the quantity of DNA protein complexes present in the fraction.

Result:
(A) The cytoplasmic fractions of high density of mouse Ehrlich ascites tumor cells and human L428 Hodgkin lymphoma cells show in dependency upon the dilution of the fraction a hybridizational signal with the consensus DNA probe.
(B) A hybridization signal with the corresponding fractions of primary mouse embryo fibroblasts or human lymphocytes from peripheral blood was not generated.

EXAMPLE 14

Detection of Human or Animal Cells with an Unlimited Proliferation or Tumor-formation Potential by Hybridizing the Consensus Probe with a Cell Lysate This experimental arrangement is a simplification of the procedure described in Example 1 and utilizes the fact that the cell lysate (without further purification of the DNA protein complexes) is free of other DNA sequences that cross-hybridize with the consensus DNA sequence.

The cells are lysed in the presence of 50 mmol/l Tris-HCl, pH 7.2, 10 mmol/l EDTA 1.5 mmol $MgCl_2$ by repeated freezing and thawing; the nuclei are then separated by centrifuging for 30 min at 6000 g. The so obtained supernatant is incubated with RNase A (20 μg/ml) for 30 min at 37° C. and then with proteinase K (50 μg/ml) for 2 h at 60° C. 15×SSC is added to the probes and the resulting DNA is denatured by heating up to 100° C. for 2 min and subsequently plotted onto a nylon membrane using the dot blot method (Sambrook et al., Molecular Cloning, Cold Spring Harbor, 2nd edition, 1989). Hybridization with the DIG-labeled consensus DNA probe is carried out as in Example 1. The hybridization signal is quantitatively determined using densitometric measuring of the autoradiograph.

Result:
(A) The cytoplasmic lysate of Ehrlich ascites cells and the one of L428 Hodgkin lymphoma cells shows a hybridization signal with the consensus probe in dependency upon the dilution of the lysate.
(B) The cytoplasmic lysate of primary mouse embryo fibroblasts or human blood lymphocytes did not generate a signal.

EXAMPLE 15

Detection of Cells with an Unlimited Proliferation or Tumor-formation Potential Using in Situ Hybridization of the Culture Cells and a Tumor Biopsy This example demonstrates the use of the consensus DNA probe to detect established cells of a human carcinoma line in vitro and of tumor cells in a mamma carcinoma biopsy. The cells of the established MCF-7 tumor lines were established by growing human mamma carcinoma in vitro an show unlimited proliferation potential and the capability of forming tumors in vivo. Normal human fibroblasts, however, cease to proliferate after 15–20 passages in the culture and then die.

MCF-7 cells (A) and normal human fibroblasts (B) are grown on DMEM medium on microscopic slides. The frozen section of a biopsy of human mamma carcinoma is applied onto a microscopic slide (C). The microscopic slides are washed briefly in PBS, and coated for 5 min with a neutral paraformaldehyde solution (5%) to fix it and then washed twice in ethanol (70%). For use in the detection of cells with the potential of forming tumors, the consensus oligonucleotide (100 pmol) (SEQ ID NO 62) in 20 μl reaction buffer (20 mmol/l potassium cacodylate, 25 mol/l Tris-HCl, pH 6.8, 5 mmol/l $CoCl_2$, 0.25 mg/ml bovine serum albumin) is labeled with 25 U terminal transferase (Boehringer Mannheim) for 20 min at 37° C. with digoxigenin-labeled ddUTP (DIG-11-ddUTP) (1 nmol) (Boehringer Mannheim). The labeled oligonucleotide is separated from the free DIG-ddUTP nucleotides by gel filtration on a P10 column (Biorad). To achieve hybridization, the microscopic slides with the fixed cells (A, B) and the tissue sections (C) are coated with 100 μl hybridization solution (50% deionized formamide, 4×SSC, 10% dextrane sulfate, 1×Denhardt's solution, 0.25 mg/ml denatured tRNA, 0.5 mg/ml denatured herring sperm DNA). The microscopic slides are incubated for 1 h at 42° C. in a humid chamber. Subsequently, the solution is removed again, the cells are coated with DIG-ddUTP-labeled consensus oligonucleotide probe (5 ng DNA in 40 μl hybridization solution) and incubated overnight at 42° C. in a humid chamber. The microscopic slides are

EXAMPLE 16

Detection of Human or Animal Cells with the Capability of Unlimited Proliferation Using the Binding of Cytoplasmic DNA Protein Complexes to the Consensus Probe This experimental arrangement allows the approximate determination of the number of cells with unlimited proliferation or tumor formation in a mixture of normal presenescent cells with limited proliferation capacity. The (labeled) consensus DNA probe of the invention is bound to DNA of cytoplasmic complexes; subsequently, the number of labeled consensus DNA molecules is determined with the aid of an immuno-reaction and compared to known standard. The method is designed such that the experimental steps can be carried out on an accordingly prepared microtiter plate.

1. Preparation of the cell lysate

A mixture of cells (a total of $10^5$ cells) of primary mouse embryo fibroblasts (MEF) and Ehrlich ascites cells (EAZ) which contain the Ehrlich ascites cells to be detected in increasing concentrations are taken up in 100 μl of 50 mmol/l Tris-HCl, pH 7.2, 10 mmol/l EDTA, 3 mmol/l $MgCl_2$; the cells are lysed by freezing and thawing twice. The nuclei are sedimented by centrifugation for 10 min at 6000 g and the supernatant is for 2 minutes exposed to ultra sound in an ultra sound bath.

2. Coating the microtiter plate

A-96-well microtiter plate that is suitable for ELISA tests is coated with streptavidin, then washed and dried. The terminus of the linear DNA in the cell lysate is labeled with biotin dUTP using a terminal transferase (42 U) (Boehringer Mannheim) in the presence of 20 mM potassium cacodylate, 25 mM Tris-HCl, pH 6.8, 5 mM CoCl$_2$, 0.25 mg/ml bovine serum albumin for 1 h at 37° C.; non-incorporated biotin dUTP is separated by means of gel filtration using a Sephadex G50 column (manufactured by Pharmacia). The biotin-labeled DNA is added to the streptavidine-coated microtiter plate and incubated for 13 min at 37° C. Subsequently, the wells of the microtiter plate are washed 3 times with PBS.

3. Detection of bound DNA protein complexes

During the oligonucleotide synthesis, the consensus DNA is labeled with digoxigenin (DIG)-dUTP and non-incorporated DIG-dUTP is separated via gel filtration on a P10 column (manufactured by Biorad). This DIG-labeled detection probe is added to the bound DNA protein complex in the microtiter plate (50 ng of consensus DNA per well) in the presence of (4×SSC, 0.5% SDS, 0.5 mg/ml denatured herring sperm DNA) and incubated for 2 h at room temperature. During this period, the detection probe hybridizes to the DNA of the bound DNA complexes. Subsequently, non-bound probe is removed by washing several times with PBS. The bound DNA probe is detected by incubating it for 1 h with an anti-DIG antibody, Fab fragments, coupled to peroxidase (150 mU/ml in PBS, 0.5 mg/ml bovine serum albumin) (Boehringer Mannheim) at 37° C. The wells are washed twice with PBS and subsequently incubated with 200 µl ABTS substrate (peroxidase substrate solution) for 1 h at room temperature. The absorbance of the precipitation in the respective wells is measured at a wavelength of 405 nm using a microplate reader. The absorbance is proportional to the amount of bound consensus DNA and, hence to the quantity of bound cytoplasmic DNA protein complexes and the quantity of Ehrlich ascites cells in the cell mixture (Table 3).

TABLE 3

Detection of human or animal cells with the capability of unlimited proliferation using the binding of cytoplasmic DNA protein complexes to the consensus probe

| Cells | | Absorbance units [mU] |
|---|---|---|
| — | — | 78 |
| MEF (10$^5$) | EAZ (10) | 102 |
| MEF (10$^5$) | EAZ (100) | 153 |
| MEF (10$^5$) | EAZ (10$^3$) | 297 |
| MEF (10$^5$) | EAZ (10$^4$) | 558 |
| MEF (10$^5$) | EAZ (10$^5$) | 1320 |

EXAMPLE 17

Detection of the DNA Protein Complex in the Serum of Tumor Patients Using the Binding to the Consensus Probe Cells with unlimited proliferation potential excrete cytoplasmic DNA protein complexes. The detection of these excreted complexes can, hence, be used to detect cells with the capability of unlimited proliferation, especially the detection of tumor cells. Moreover, the serum of many tumor patients contains DNA protein complexes in increased titers as compared to the sera of healthy test subject. The here described experimental arrangement is suitable to determine the titer of the DNA protein complexes in serum in order to show presence of cells with unlimited proliferation potential or the capability of tumor formation in patients.

Two alternative methods are available.

Method A

The basis for this method is the labeling of linear DNA molecules of the DNA protein complexes in the serum of tumor patients at its terminus with biotin, binding the biotin-streptavidine bridge to a microtiter plate, and detecting the bound DNA protein complexes with the aid of a DIG-labeled consensus DNA probe; a quantification is then achieved in a comparison with the standard.

A1. Binding the serum DNA complexes to the microtiter plate

The terminus of the DNA protein complex in the serum of patients is labeled with the biotin ddUTP using a terminal transferase; subsequently, non-incorporated biotin ddUTP nucleotides are separated via gel filtration using a Sephadex G50 column (manufactured by Pharmacia). The microtiter plate is coated with streptavidine as described in Example 4. The serum which contains the biotin-labeled protein complexes is added into the microtiter plate and incubated for 30 min at room temperature. Subsequently, the microtiter plate is washed 3 times with PBS.

A2. Detecting the bound DNA protein complexes

During synthesis, the consensus oligonucleotide is labeled via incorporation of DIG-dUTP. The DNA protein complexes bound on the surface of the microtiter plate are incubated for 1 h at 42° C. with portions of 50 ng of DIG-labeled consensus DNA in the presence of hybridization solution (4×SSC, 0.5% dextrane sulfate, 1×Denhardt's solution, 0.25 mg/ml denatured tRNA, 0.5 mg/ml denatured herring sperm DNA). Subsequently, the wells are washed 3 times with PBS and the bound DIG consensus DNA is detected using an anti-DIG ELISA test. The wells are incubated for 1 h at 37° C. with an anti-DIG antibody, Fab fragments coupled to peroxidase (150 mU/ml in PBS, 0.5 mg/ml bovine serum albumin) (Boehringer Mannheim). The wells are washed twice with PBS and subsequently incubated for 1 h at room temperature with 200 µl ABTS substrate (peroxidase substrate solution). The absorbance is directly proportional to the quantity of bound consensus probe and, hence to the quantity of DNA protein complexes in the serum.

Result:

(A) The absorbance in the sera of healthy test subjects is <50 mU up to 200 mU.

(B) Sera of tumor patients (mamma carcinoma, colon carcinoma) show an absorbance of 300 mU to >600 mU.

The increased titer of the DNA protein complexes in the serum as compared to the titer in the serum of healthy patients demonstrates the presence of cells with unlimited proliferation or tumor formation potential.

TABLE 4

Detection of DNA protein complexes in the serum of tumor patients via binding of the consensus probe (method A)

| Serum No. | Tumor/healthy | Absorbance units [mU] |
|---|---|---|
| N-1 | healthy | 130 |
| N-2 | healthy | 30 |
| N-3 | healthy | 70 |
| N-4 | healthy | 60 |
| N-5 | healthy | 160 |
| TU-1 | colon carcinoma | 460 |
| TU-2 | colon carcinoma | 330 |
| TU-3 | colon carcinoma | 500 |
| TU-4 | colon carcinoma | 610 |
| TU-5 | colon carcinoma | 400 |
| TU-6 | mamma carcinoma | 570 |

TABLE 4-continued

Detection of DNA protein complexes in the serum of tumor patients via binding of the consensus probe (method A)

| Serum No. | Tumor/healthy | Absorbance units [mU] |
|---|---|---|
| TU-7 | mamma carcinoma | 330 |
| TU-8 | mamma carcinoma | 340 |

Method B

This method is based on the fact that DNA protein complexes adhere to carrier membranes where they can be detected with the consensus DNA probe.

The serum of tumor patients and healthy test subjects is incubated for 1 h at 60° C. in the presence of 0.1% SDS and 100 μg/ml proteinase K. Subsequently, the same quantity of a solution consisting of 15% formaldehyde, 20×SSC is added and the mixture is incubated for 20 min at 80° C.; the sample is then applied onto a nylon membrane (Hybond N, Amersham Buchler) and a dilution series (1:10, 1:100, 1:1000, 1:10,000). The membrane is dried and then hybridized with 500 ng of DIG-labeled consensus DNA probe for 4 h at 42° C. in hybridization solution (50% deionized formamide, 4×SSC, 10% dextrane sulfate, 1×Denhardt's solution, 0.25 mg/ml denatured tRNA, 0.5 mg/ml denatured herring sperm DNA). The membrane is washed 3 times for 2 min in 0.5×SSC, 0.1% SDS at room temperature, and the bound DIG-labeled DNA probe is detected with the aid of an anti-DIG antibody. The membrane is incubated at 37° C. for 1 h with an anti-DIG antibody, Fab fragments coupled to alkaline phosphatase (150 mU/ml in PBS, 0.5 mg/ml bovine serum albumin) (Boehringer Mannheim). The membrane is washed twice, incubated with CSPD (AP substrate solution) for 15 min at 37° C., and exposed on an x-ray film. The blackening of the film is proportional to the quantity of bound consensus DNA probe and, hence, the quantity of DNA protein complexes present in the serum. The blackening of the film is measured with a densitometer and compared to the one of the standard or of sera of healthy patients. An increased titer of bound consensus probe, in a comparison to healthy patients, indicates that the patient's serum contains an increased amount of DNA protein complexes and, hence, cells in the body tissue that are capable of unlimited proliferation and tumor formation.

Result:

(A) An absorbance of <1000 U (densitometric units) is measured in the sera of healthy test patients.

(B) Sera of tumor patients (mamma carcinoma, colon carcinoma, Hodgkin lymphoma) show an absorbance of 1500 U to >3000 U.

The increased titer of the DNA protein complexes in the serum as compared to the titer in the serum of healthy test patients indicates the presence of cells of unlimited proliferation or tumor formation potential.

TABLE 5

Detection of DNA protein complexes in serum of tumor patients using the binding to the consensus probe (method B)

| Serum No. | Tumor/healthy | Absorbance units [mU] |
|---|---|---|
| N-1 | healthy | 800 |
| N-2 | healthy | 185 |
| N-3 | healthy | 427 |
| N-4 | healthy | 366 |
| N-5 | healthy | 976 |
| TU-1 | colon carcinoma | 2806 |
| TU-2 | colon carcinoma | 2013 |
| TU-3 | colon carcinoma | 3050 |
| TU-4 | colon carcinoma | 3721 |
| TU-5 | colon carcinoma | 2440 |
| TU-6 | mamma carcinoma | 3477 |
| TU-7 | mamma carcinoma | 2013 |
| TU-8 | mamma carcinoma | 2074 |

What is claimed is:

1. A nucleic acid fragment of no more than 592 nucleotides in length or nucleic acid fragment analog of no more than 592 nucleotides in length having a sequence as shown in one of SEQ ID NO: 2–SEQ ID NO: 28 or SEQ ID NO: 30–SEQ ID NO: 61.

2. A nucleic acid fragment of no more than 592 nucleotides in length or nucleic acid fragment analog of no more than 592 nucleotides in length comprising a subsequence of at least 15 nucleotides in length, wherein the subsequence can form a DNA-protein complex which is suitable for detecting human or animal malignant tumor cells and wherein the subsequence is selected from the group consisting of
   (a) a subsequence contained in a sequence as shown in one of SEQ ID NO: 2–SEQ ID NO: 28 or SEQ ID NO: 30–SEQ ID NO: 62,
   (b) a subsequence that is obtained by linking two subsequences, wherein each of the two subsequences is selected independently from the sequences shown in SEQ ID NO: 1–SEQ ID NO: 45, SEQ ID NO: 46–SEQ ID NO: 58 or SEQ ID NO: 59–SEQ ID NO: 62,
   (c) a subsequence which codes for the same amino acid sequence encoded by one of (a) or (b) and
   (d) a subsequence which is completely identical or completely complementary to one of (a) or (b).

3. A nucleic acid fragment of no more than 592 nucleotides in length or nucleic acid fragment analog of no more than 592 nucleotides in length comprising a subsequence of between 16 and 100 nucleotides in length, wherein the subsequence can form a DNA-protein complex which is suitable for detecting human or animal malignant tumor cells and wherein the subsequence is selected from the group consisting of
   (a) a subsequence contained in a sequence as shown in one of SEQ ID NO: 2–SEQ ID NO: 28 or SEQ ID NO: 30–SEQ ID NO:62,
   (b) a subsequence that is obtained by linking two subsequences, wherein each of the two subsequences is selected independently from the sequences shown in SEQ ID NO: 1–SEQ ID NO: 45, SEQ ID NO: 46–SEQ ID NO: 58 or SEQ ID NO: 59–SEQ ID NO: 62,
   (c) a subsequence which codes for the same amino acid sequence encoded by one of (a) or (b) and
   (d) a subsequence which is completely identical or completely complementary to one of (a) or (b).

4. A method of obtaining a DNA which is indicative of a human or animal malignant tumor cell when complexed with a protein, the method comprising
   isolating a DNA-protein complex by isolating a mitochondria-free fraction of the cytoplasm of neoplastically transformed human or animal cells, said fraction having a density of about 1.82–1.89 g/cm$^3$ in a cesium chloride gradient, and thereafter isolating said complex from said fraction,
   identifying or verifying the presence of the protein of said isolated DNA-protein complex by treating the complex with DNAse I and chromatographically isolating the protein,
   ligating into a cloning vector the DNA of said isolated DNA-protein complex,
   cloning the DNA in a host cell and
   thereafter isolating the cloned DNA.

5. A method of obtaining a DNA which is indicative of a human or animal malignant tumor cell when complexed with a protein, the method comprising
   isolating a DNA-protein complex by isolating a nuclei-free fraction of the cytoplasm of neoplastically transformed human or animal cells, said complex having a density of about 1.86 g/cm$^3$ in a cesium chloride gradient, and thereafter isolating said complex from said fraction,
   identifying or verifying the presence of the protein of said isolated DNA-protein complex by treating the complex with DNAse I and chromatographically isolating the protein,
   ligating into a cloning vector the DNA of said isolated DNA-protein complex, cloning the DNA in a host cell and
thereafter isolating the cloned DNA.

6. A method of obtaining a DNA which is indicative of a human or animal malignant tumor cell when complexed with a protein, the method comprising
isolating a DNA-protein complex from a mitochondria-free fraction of the cytoplasm of neoplastically transformed human or animal cells, said fraction having a density of about 1.82–1.89 g/cm$^3$ in a cesium chloride gradient,
identifying or verifying the presence of the protein of said isolated DNA-protein complex by treating the complex with DNAse I and chromatographically isolating the protein, and
replicating the DNA of said isolated DNA-protein complex.

7. A method of obtaining a DNA which is indicative of a human or animal malignant tumor cell when complexed with a protein, the method comprising
isolating a DNA-protein complex from a nuclei-free fraction of the cytoplasm of neoplastically transformed human or animal cells, said complex having a density of about 1.86 g/cm$^3$ in a cesium chloride gradient,
identifying or verifying the presence of the protein of said isolated DNA-protein complex by treating the complex with DNAse I and chromatographically isolating the protein, and
replicating the DNA of said isolated DNA-protein complex.

8. A method of obtaining a DNA which is indicative of a human or animal malignant tumor cell when complexed with a protein, the method comprising hybridizing a sequence as shown in one of SEQ ID NO: 2–SEQ ID NO: 28 or SEQ ID NO: 30–SEQ ID NO: 61 with a human or animal genetic library to produce a hybridized DNA sequence and thereafter isolating the hybridized DNA sequence from the genetic library.

9. The method of claim 8, wherein the genetic library is a genomic genetic library.

10. The method of claim 8, wherein the genetic library is a DNA genetic library.

11. A method of obtaining a DNA which is indicative of a human or animal malignant tumor cell when complexed with a protein, the method comprising
hybridizing to a genetic library an oligonucleotide molecule which hybridizes with a subsequence according to claim 2, and thereafter replicating the hybridized subsequence in a polymerase chain reaction.

12. The method of claim 11, wherein the oligonucleotide molecule is between 20 and 30 nucleotides in length.

13. A method of cloning a DNA which is indicative of a human or animal malignant tumor cell when complexed with a protein, the method comprising hybridizing an oligonucleotide molecule which is completely complementary to a sequence as shown in one of SEQ ID NO: 2–SEQ ID NO: 28 or SEQ ID NO: 30–SEQ ID NO: 61 to a genetic library to produce a hybridized sequence and enzymatically replicating the hybridized sequence in a polymerase chain reaction.

14. The method of claim 13, wherein the oligonucleotide molecule is between 20 and 30 nucleotides in length.

15. A method of obtaining a DNA which is indicative of a human or animal malignant tumor cell when complexed with a protein, the method comprising chemically synthesizing a sequence as shown in SEQ ID NO: 2–SEQ ID NO: 28, or SEQ ID NO: 30–SEQ ID NO: 61, or a portion thereof which is specific to a nucleic acid fragment according to claim 1.

16. A method of detecting human or animal malignant tumor cells, comprising
hybridizing a DNA fraction of human or animal cells with a DNA to form a hybridizing complex, wherein said DNA is obtained by enzymatically replicating the DNA of a DNA-protein complex, said DNA-protein complex being obtainable by isolating a mitochondria-free fraction of the cytoplasm of neoplastically transformed human or animal cells, said mitochondria-free fraction having a density of about 1.82–1.89 g/cm$^3$ in a cesium chloride gradient, and thereafter isolating said DNA-protein complex from said mitochondria-free fraction, and
detecting the hybridized complex to indicate the presence of human or animal malignant tumor cells.

17. A method of detecting human or animal malignant tumor cells, comprising
hybridizing a DNA fraction of human or animal cells with a DNA to form a hybridized complex, wherein said DNA is obtained by enzymatically replicating the DNA of a DNA-protein complex, said DNA-protein complex being obtainable by isolating a nuclei-free fraction of the cytoplasm of neoplastically transformed human or animal cells, said DNA-protein complex having a density of about 1.86 g/cm$^3$ in a cesium chloride gradient, and thereafter isolating said DNA-protein complex from said nuclei-free fraction, and
detecting the hybridized complex to indicate the presence of human or animal malignant tumor cells.

18. A method of detecting human or animal malignant tumor cells, comprising
hybridizing a DNA-protein complex from a nuclei free fraction with a nucleic acid fragment or nucleic acid fragment analog having a sequence as shown in one of SEQ ID NO: 1–SEQ ID NO: 62, or a completely complementary sequence thereof, to form a hybridized complex, and
detecting the hybridized complex to indicate the presence of human or animal malignant tumor cells.

19. A method of detecting human or animal malignant tumor cells, comprising hybridizing a DNA-protein complex from a nuclei free fraction with a nucleic acid fragment or nucleic acid fragment analog having a sequence as shown in one of SEQ ID NO:2–SEQ ID NO: 28 or SEQ ID NO: 30–SEQ ID NO: 61 to form a hybridized complex, and detecting the hybridized complex to indicate the presence of human or animal malignant tumor cells.

20. A method of detecting human or animal malignant tumor cells, comprising
replicating nucleic acid of a nucleic acid fraction or cell lysate of human or animal cells by using an oligonucleotide molecule which hybridizes with a sequence of at least 15 nucleotides in length, wherein the sequence is selected from the group consisting of
(a) a sequence contained in a sequence as shown in one of SEQ ID NO: 2–SEQ ID NO: 28 or SEQ ID NO: 30–SEQ ID NO: 62,
(b) a second sequence that is obtained by linking two subsequences, wherein each of the two subsequences is selected independently from the sequences shown in SEQ ID NO: 1–SEQ ID NO: 45, SEQ ID NO: 46–SEQ ID NO: 58 or SEQ ID NO: 59–SEQ ID NO: 62,
(c) a sequence which codes for a same amino acid sequence as encoded by one of (a) and (b) and
(d) a sequence which is completely identical or completely complementary to one of (a) and (b), to a genetic library to produce in a polymerase chain reaction, hybridizing said replicated nucleic acid with a nucleic acid or nucleic acid analog to produce a hybridized complex and detecting said hybridized complex to indicate the presence of human or animal malignant tumor cells.

21. A method of detecting in-situ human or animal malignant tumor cells, comprising treating under hybridizing conditions whole cells or tissue of human or animal cells with a nucleic acid fragment or nucleic acid fragment analog of claim 2 to form a hybridized complex, and detecting the hybridized complex to indicate the presence of human or animal malignant tumor cells.

22. A method of detecting human or animal malignant tumor cells, comprising replicating nucleic acid of a DNA-protein complex from a nuclei free fraction of human or animal cells by using an oligonucleotide molecule which hybridizes with a nucleic acid fragment or nucleic acid fragment analog according to claim 2 in a polymerase chain reaction, hybridizing said replicated nucleic acid with a nucleic acid fragment or nucleic acid fragment analog to produce a hybridized complex and detecting said hybridized complex to indicate the presence of human or animal malignant tumor cells.

23. A DNA-protein complex, which is obtainable by isolating a mitochondria-free fraction of the cytoplasm of neoplastically transformed human or animal cells, said fraction having a density of about 1.82–1.89 g/cm$^3$ in a cesium chloride gradient, and thereafter isolating said complex from said fraction.

24. A DNA-protein complex, which is obtainable by isolating a nuclei-free fraction of the cytoplasm of neoplastically transformed human or animal cells, said complex having a density of about 1.86 g/cm$^3$ in a cesium chloride gradient, and thereafter isolating said complex from said fraction.

25. A DNA fragment of no than 592 nucleotides in length suitable for detecting human or animal malignant tumor cells, said DNA fragment being obtainable by cloning or enzymatically replicating a DNA fragment of said DNA-protein complex of claim 23 which contains a sequence as shown in one of SEQ ID NO:2–SEQ ID NO:28 or SEQ ID NO:30–SEQ ID NO:61, or a completely complementary sequence thereof.

26. A DNA fragment of no than 592 nucleotides in length suitable for detecting human or animal malignant tumor cells, said DNA fragment being obtainable by cloning or enzymatically replicating a DNA fragment of said DNA-protein complex of claim 24 which contains a sequence as shown in one of SEQ ID NO:2–SEQ ID NO:28 or SEQ ID NO:30–SEQ ID NO:61, or a completely complementary sequence thereof.

* * * * *